US006410325B1

(12) United States Patent
Bennett et al.

(10) Patent No.: US 6,410,325 B1
(45) Date of Patent: Jun. 25, 2002

(54) ANTISENSE MODULATION OF PHOSPHOLIPASE A2, GROUP VI (CA2+-INDEPENDENT) EXPRESSION

(75) Inventors: C. Frank Bennett, Carlsbad; Susan M. Freier, San Diego; Andrew T. Watt, Vista, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/851,896

(22) Filed: May 9, 2001

(51) Int. Cl.[7] .......................... C12Q 1/68; C07H 21/04; C12N 15/85
(52) U.S. Cl. .................. 435/375; 435/6; 435/91.1; 435/366; 536/23.1; 536/24.31; 536/24.33; 536/24.5
(58) Field of Search .................. 435/6, 325, 366, 435/375, 91.1; 536/23.1, 24.5, 25.3; 514/44

(56) References Cited

U.S. PATENT DOCUMENTS 5,801,154 A * 9/1998 Baracchini et al.
5,951,455 A * 9/1999 Cowsert

OTHER PUBLICATIONS

Andrea D. Branch, A good antisense molecule is hard to find, TIBS 23—Feb. 1998.*
Flanagan et al., Nature Biotech 17, Jan. 1999, pp. 48–52.*
Atsumi et al., Fas–induced arachidonic acid release is mediated by Ca2+–independent phospholipase A2 but not cytosolic phospholipase A2, which undergoes proteolytic inactivation, J. Biol. Chem., 1998, 273:13870–13877.
Balsinde et al., Antisense inhibition of group VI Ca2+–independent phospholipase A2 blocks phospholipid fatty acid remodeling in murine P388D1 macrophages, J. Biol. Chem., 1997, 272:29317–29321.
Balsinde et al., Function and inhibition of intracellular calcium–independent phospholipase A2, J. Biol. Chem., 1997, 272:16069–16072.
Cupillard et al., Cloning, chromosomal mapping, and expression of a novel human secretory phospholipase A2, J. Biol. Chem., 1997, 272:15745–15752.
Dennis, Diversity of group types, regulation, and function of phospholipase A2, J. Biol. Chem., 1994, 269:13057–13060.
Dennis, The growing phospholipase A2 superfamily of signal transduction enzymes, Trends Biochem. Sci, 1997, 22:1–2.
Larsson Forsell et al., On the expression of cytosolic calcium–independent phospholipase A2 (88kDa) in immature and mature myeloid cells and its role in leukotriene synthesis in human granulocytes, FEBS Lett., 1998, 434:295–299.
Larsson et al., Multiple splice variants of the human calcium–independent phospholipase A2 and their effect on enzyme activity, J. Biol. Chem., 1998, 273:207–214.
Ma et al., Pancreatic islets express a Ca2+–independent phospholipase A2 enzyme that contains a repeated structural motif homologous to the integral membrane protein binding domain of ankyrin, J. Biol. Chem., 1997, 272:11118–11127.
Ma et al., Human pancreatic islets express mRNA species encoding two distinct catalytically active isoforms of group VI phospholipase A2 (iPLA2) that arise from an exon–skipping mechanism of alternative splicing of the transcript from the iPLA2 gene on chromosome 22q13.1, J. Biol. Chem., 1999, 274:9607–9616.
Tang et al., A novel cytosolic calcium–independent phospholipase A2 contains eight ankyrin motifs, J. Biol. Chem., 1997, 272:8567–8575.
Zhou et al., Apoptosis in insulin–secreting cells. Evidence for the role of intracellular Ca2+ stores and arachidonic acid metabolism, J.Clin. Invest., 1998, 101:1623–1632.

* cited by examiner

Primary Examiner—John L. LeGuyader
Assistant Examiner—M Schmidt
(74) Attorney, Agent, or Firm—Licata & Tyrrell P.C.

(57) ABSTRACT

Antisense compounds, compositions and methods are provided for modulating the expression of Phospholipase A2, group VI (Ca2+-independent). The compositions comprise antisense compounds, particularly antisense oligonucleotides, targeted to nucleic acids encoding Phospholipase A2, group VI (Ca2+-independent). Methods of using these compounds for modulation of Phospholipase A2, group VI (Ca2+-independent) expression and for treatment of diseases associated with expression of Phospholipase A2, group VI (Ca2+-independent) are provided.

13 Claims, No Drawings

```
                        SEQUENCE LISTING

<160> NUMBER OF SEQ ID NOS: 89

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 70000
<212> TYPE: DNA
<213> ORGANISM: Homo sapiens
<220> FEATURE:
```

<400> SEQUENCE: 3

```
tataaccagt atggccctgt acaaatacat gattttactg ttgggtcata g gcagaattg      60
aaaggagtgg aaagggaaag ggctagaatg agaagacaag gagagaagga t gagcaggag     120
gtcccttgtc tttcagtgta tcatttggca gtgtttgttc atcacctctt g tgagtcagg    180
ctcttctgta tatgttctct tcaccattca ttcagtcatc gtttatctaa c aaatattta    240
cggactgtct gatgttctag ctacccttg tgtggccaa tgatattctc a cttcacatg      300
agaaaaagag ggcgcatgag ttgcttgagg tcacaccgat gaggttgaag c tggaatctg    360
acaccagagc ctgtgtgatt gtcctgatgt gtaaggtttg ctactgttta g gacacttct   420
tgttccttcc gtggattact ttcttgttac atgagagact ccccaaaagg g agtttccct   480
cttactcagc agaatgacat cactaagaga tacagaaagg agaaatttaa a tactctgtg   540
tgtgtgtgtg tgtgtgtgtg tgtgtgtgtg tgtgtgtgtc tgcagacatc t attgggtgt  600
gtgtgctggg ggaagtaggt aggcaaggag taaggggccg tagtgaagag t gtgttacaa  660
acttcacttt gtagagggtg gctccctggg agaatatgtt ctgtgtcttt c acagtggat  720
tttgataggg tcatgtctta aatgcctctt ctcgttttcg gatggtgatc t catccagtc  780
ttatttcttt aagtgccgtc tctattctgt cagcccacaa atttatatcc c cagtccagt  840
ccagaccttt ccctggaatg acatactcaa atctagttgc ttactcagca c ctcaaactt  900
aggcttttca aacttgaagt atttatttat tgatttattt atttttttgag a cagagtctc  960
actctgtcac ccaggctgga atgcaatggc acgatctcgg ctcactgcaa c ctccacctc 1020
ctgattctcc tgcctcagcc tcccaagtag ctgggattac aagcatgcgc c atcatgccc 1080
aactaatttt tgtatttttg tagaggcggg gtttcaccgt gttggccagg c tggtctcga 1140
actcctgatc tcaagtgatc cacctgcctt ggcctcccaa agtggtggga t tacaggtgt 1200
gagccaccgc gccaggcctc aaacttaaga gtttagaatt gagctcctgt t agttctgcc 1260
ctccatccct gacccactc ttcaccaaaa catgtccctc ccactctctt t ctcatctta  1320
ggacatagga gtattgttca ttcagttgct caggtcaaag ctgtgagatt a tctatgatg 1380
cctctctgtt tcttacccca cacccagcca gagtgatctt gttaaaatgt t gtttctttg 1440
cagtggcctc tcctctcatg gcacatgcct ggcccctgt tgcctctctg a tgtcactgg  1500
cttccttgct tttcctggaa ctcgctaaac atgttccagc cccatggcct t tgcacacgc 1560
tctctttgcc tagctattca tatgactttc atctctctcc atcaggtatt t atttaagat 1620
caatttcttg gtgaagactt ctctcctcac ccaatctaaa atttcactct c cacctcagc 1680
acttcctatc cccattctct ggttttttctc ctcagtagtt aattgtcatc t aaaacctttt 1740
gtaaatattt acctgtttat cttctttatt attagtagct ctgtctaaaa t ataagttcc  1800
aggatgtcag ggattttgtg gggttttttt tggttggttg gttgttttgg t tttgagaca  1860
gggtctcact ctgttgccca ggctggagcg cagtggtgcg atctcagctc a ctgcagcct  1920
ccgcctcctg ggtttgagtg attctcccac ctcagtctcc caggaagctg g aattacagg  1980
tgcacgccac cacacccagc taattttttgt attttttggt agagatgggg t ttcactatg 2040
ttggccaggc cggtcttgaa ctcttgacct caagtgatcc accgcctcg g cctcccaaa  2100
gttctgggat tactggtgtg agccaccgcg cccggccttg ttttgtttta a gacagggtc  2160
tcactgtcgc tcaggctgga ttgcagtggc acaatcacag ctcactgcag c ctcgacctg  2220
ctagacttaa gcaatccccc cacctcagcc acctagtag ctgggactta c aggcatgag  2280
```

-continued

| | | | | | |
|---|---|---|---|---|---|
| agataccatg | cctgggtaat | tgttaagttt | ttgtagaggt | gaggtctcac t | atattaccc 2340 |
| aggctggtct | caaagtcctg | agcttaagtg | atcctccttc | cttggcctcc t | aaagtgctg 2400 |
| ggattacagg | agtgaactgc | cgtgcctgac | cagtctgttt | tgtttacgat t | gtatcctca 2460 |
| gcggttagaa | caatgcctgc | cacaatccat | ctcagtaaat | atttgtggag t | gagtcataa 2520 |
| catgggccac | actgtaccgt | gccaccagcc | caaagatctc | ttaaagtcac c | cctgtctca 2580 |
| tgtgcttggg | agctccagtg | acagtttcgg | ggcagtttgc | ttccagctgt g | gtccagcca 2640 |
| agcggagtga | atgaaagaga | tgcttttttcc | ttttgtgaaa | ggacgttttg c | tctggctca 2700 |
| cgtgagcagc | agtgcatttt | gagacgaggg | ccttggcttt | tggaatctaa g | agcctgttg 2760 |
| agcaagcctc | gctcagccac | cttctttcag | cttttctcctg | aaggcagttt g | aggattaag 2820 |
| agcctgatgc | tctggattcc | acctaattgg | gttcagatcc | tggcaaactg t | gtaacctgt 2880 |
| gccccagttt | cctgtgtaat | gtggagagac | ctggaccttt | tcttacaggt g | tttggaggg 2940 |
| ttaaatgtgg | caattcggcc | gggcgcagtg | gctcatgcct | gtaaccccag c | actttggga 3000 |
| ggtggaggtg | ggcggatcac | cggaggtcag | gagttcaaga | ccagcctggt t | aacatggtg 3060 |
| aaaccccgtt | tctactaaaa | atacaaaaaa | ttagccgagt | gtggtggtgc g | cgcctgtaa 3120 |
| tcccagctag | tctggagact | gaggcaggag | aatcgcttga | acccgggagg c | agaggttgc 3180 |
| agtgagccaa | gatcacgcca | ttgcactcca | gcttgggcaa | caagagtgaa a | ctctgtctc 3240 |
| aaaaaaaaaa | aaaaaaaaaa | agtggcaatt | tacccgaaac | tgtggtgaag c | gtctggcgc 3300 |
| cctgtgggtg | ctgggcagca | gtgggtgctg | atggggtgtg | aggggatggg a | tcaagccct 3360 |
| ttcccactaa | cttaggaaag | aggttggaat | gagctgggt | cagagggaac a | tttgcgggg 3420 |
| acattttgcc | gggaggctgc | cttggaggtt | cagaggctca | gatgacccct g | tgttcattc 3480 |
| agtgttttct | cacccacaga | ttgagcacct | gctgtgtggc | cagccctttg c | ctagtgctg 3540 |
| ttcaagagtc | agaggacata | ggcaggcaat | cccccaccac | aacctgccac c | ccatttcct 3600 |
| ctcttgggc | cttgatttct | ccacatgcca | aacagggaga | atgattgcac c | ttccttgtt 3660 |
| tctttttttt | tttttttgag | acagtctcac | tttgtcatcc | aagctttagt g | cagtggcat 3720 |
| gatctcggct | cactgcagcc | tctgcctctc | gggttcaaag | attctcctgc t | tcagcctcc 3780 |
| caagtagctg | tgattatagg | cacccaccat | cacgccaggc | taattttttt t | gtagttta 3840 |
| gtagagatgg | ggtttttttc | tcacacgttg | gccaggctgg | tcttgaactt c | tgacctcag 3900 |
| gtgatctgcc | catctcaccc | tcccaaagtg | ctgggattac | aggtgtgagc c | accgcgccc 3960 |
| ggctgcgcct | tccctgtttc | tttgtgagct | tggaggtgga | tcacaagtgt g | aaacccttt 4020 |
| gccaaccgtg | aggcatggtg | gccttgtgag | aggacggagg | ccgtgtgtg g | tggcatgct 4080 |
| cccgtgctgt | gtggcacaga | cggagctaca | ggaaggaagt | tggggcagct t | ggcactctg 4140 |
| agtggaccct | gagtttccag | cctgctctgt | cttgactggg | tgggaggagg g | tgctcagga 4200 |
| gggtgtcact | gctgccaggt | tctgctgcca | ggaccatcca | acagttgttc c | aatcatggg 4260 |
| acatcctgtc | gtcagcagct | ggggctcgtg | aggcctgatt | tccacctcgg g | cagttctgt 4320 |
| gtgtgctcct | ggaatccccc | acgtggccaa | gcctgtgagg | tctgcttcct g | cctgctgc 4380 |
| ctgtgggttc | ctgtcacgca | cctctcgggc | agctgtccgg | ctcctctgct c | tcggcttag 4440 |
| tcaagaagga | agcagaaggc | ttggagtctt | tcctgcttgg | actaggagtg a | gctcagcct 4500 |
| aagtgccctg | actatatata | aagctgaact | ttccagaccg | aagcctgggg a | tggatcagt 4560 |
| ccgatcactt | agggccgctc | ctgaaggagt | gcaggtgcta | gatacaggtt c | tcccggtgg 4620 |
| aggagcgaac | cccttgtggg | ccgttagcta | ctggtgggat | ttgagcatgg t | atttcccta 4680 |

```
tccgttgtgg agaggagcat ggcagctcag agtgggtggg aacagtgtgt g gtccctgtt    4740
atcaccttca agggaataaa gtgtgtctgg gggcttcaga ggtgctggcc c catgggctt    4800
ataggtggtt cattcattca ttctcattca ttcattcacc aaacttatta a acacccact    4860
gtgagtcagg aacatcatgc caggtgctta gggaaacaaa tcaaagcggg t tgggtgagc    4920
agcccaagcc aacagatgca cccccattct cacatggtgt gtgttcctgt g ggctgggcc    4980
ctgggtggtg tggggtgctg gggagaagag gaaggcacac caggctgcag g gcggaggtg    5040
cgggtatgaa ttttcagagg agatggcacc tgagctgtat cttcatggat a agaagagat    5100
ttgttcattt gtcctttgtg gagcacacat tcaggttaag aaagtgggga g gatgggcta    5160
cgctgatgga gcgtatgtgt ggtatcccca agtgcactga gacacgagtt t gacgtgttc    5220
tgggaagatc gatggtgcgg cgtggctgga gtagaggtga gggatgagtt g gagggtgga    5280
gttgggccag ctctcatgga tgctggagtc tgggctttcc ctgggaggtc a tggggcgcc    5340
actgccaggg gtcagcaggg agacctgcag ctggatttgc atcgtacagt g ggcatggag    5400
gggtgtcagg ctggggttggg aaccgtgcag gctggaaggg cactctggtg c tctgagcat    5460
tcagagggggg cagctgggcc ttgaaggatg agcagggggct ccagcaggaa c tggagagcg    5520
cattccaggg aggacgcaag tgcaggcccc tttcactaca gaaaagcagt t ttcacacag    5580
accttccaaa ggggaggaga ggggactgcc tgggcctggc agctgcggca g gtagcagca    5640
atcagagggc agggaccgct cctcccgtgc ctgagacctg cccagggtcc t tcagggaat    5700
tcgtagctga ggaggaacca gattttttggg actgagttct ccctcaccac c cgctctgag    5760
ccaccctctt ggtcccttgt cctctactgc acttcttccg gggcttggct c ctcgtcatg    5820
agaggagctt ccctgggcat ggcgaggggc gtgactgaca tagcagccct g gacaagtgg    5880
ctccaggtga cctgtgttca cgttgatcac agcactaacc acggcccctc c tctcagcac    5940
cttcccctct cgagccgtcc agtcccagtg aaaatgctca ccgttcatgg g tgggctgag    6000
caagcccctg atctctgcct tcctccgtgt tctgatctgc ttcatctgct g tgaaggcct    6060
ctcgccattt ccccgctgg caaactcctg ttcttcctgg aaagttcagc t aaaaagtca    6120
tcccctttag gggtccttcc ctcagggggac cgtgcacttg gcgagacagg g actggtctt    6180
gggtctctct gttgactgtt ttatgaaccc aggtagtcac ttccagggaa c tcatcagag    6240
atgctaccat tggctccaat ctccctctgt tcccactcga ggttttttgt t tcttcgttt    6300
gttttttcttt cttttctttt ttttgagaca gagtctcgct ctcgcccagg c tggagtgca    6360
gtgacatgat ctcggctcac tgcaagctcc gcctcccggg ttcacgccat t ctcctgcct    6420
cagcctcccg aatagctggg actacaggca cccgccacca cgcccagcta a ttttttttg    6480
tatttttagt agagacgggg tttcaccatg ttagccagga tggtctcaat c tcctgattt    6540
cgtgatccgc ccgccttaac ctcccaaagt gctgggatta caggcgtgag c cactgcgcc    6600
cagcccgttt gttttttgttt tttggtggac atcaacttta atttgccctt t gttttgttt    6660
tgttttttgag gcagggtctt gctctgtctc ccaggctgga gtgcagtagt g caatcttgg    6720
ctcactgcag tctcgacctc aagaggatca agcaatcctc ttgccttagc c tcccgagta    6780
gctgggacca caggcgcaca ccaccatgcc cagctaattt tatttatat t ttgtagaga    6840
cagggttttg ccatgttccc caggctggtc tcaaattcct gggctcaagc a atccgtctg    6900
cctcagcctc ccaaaatgct ggaattacag gcacagccca ctgtgcccgg c cttaatttg    6960
cccttttgaac atgtacaatt cagggcctct ctgggcctca gtttcttgat c tctgagatg    7020
```

```
ggaagatggg ataataatac ttgttcctcc cgtccttcag ctcctccagg g gaccctcac    7080 accagcacac tctctgtcag tcttccctca atgaacccag caggcaagct t ggttttgac    7140 agaggatggg tgagcagaga taaggaaaac ggccagaaat atctggcttc c ctcagcagg    7200 ggcaccaaaa ttggtacctg gaaattgcct ggcttggaca ggcagaattg t cactgtcaa    7260 cccccaccac caaaggtctt gggtctttgt ctttctgctt gtggtgtttg a gagagctgc    7320 ttgacacagc cgaggtgcgg tctgtgtcag gtgacctggg catcctgggg g tgcagggag    7380 aagcccaggt aaggaggagg aggggccggt catcagtggg gaaaagtgat t gtctacccc    7440 acgggaaggt caagggtagg acgctgtgag aagccagggg gagagatgaa g tgaggcatg    7500 atgcggggggg ccctcatcca ccatccccct cttgcagctg tgctgggaag a gcctaggct    7560 ccagggtcca aggtggcagg gacagaagga agcacgtgtg agcactttct c cctgctggc    7620 ccgccttcct ggttggcaat gccgtgagtg ttccaggatg tggccccgtg g ctgtcattt    7680 cctttcttcc acctagtgat aacaatggcc actgtttgtg tgcccacagt c ggcctgtgt    7740 cccagacacc ttccctccat tgcgtcatct cgtcctcctg cctaccctga a ggctggatg    7800 ccagccaagc ctgtcgtttc tgtggccatg ctgtcgtggg tgtgtggggg g catcccta    7860 gccccaggct ctggtggggg gtacacaggc tgggccattg acgaaggggt g tgtggaatc    7920 tttctttgat ttcactgcac ccctggtgac tttctccctc aatctgaggc t catgggtgc    7980 tggatgctct tgactctctg cccttcctgg gcgcacccct ccgcgtccct g tgggcccgt    8040 cctcggggta gcctctctgc gctcttccag gccaggcctg agtcccacag g tccccatct    8100 tcccggctgc agcccccaga ggctcagcct atactgctac ttcctttgaa a actataatc    8160 gctttacata gcatctggaa aatagggaaa aggaaaaaac aaaagcccat a aacccagca    8220 ccctcatcta ctcaatggca tgttttctgt cagtctatct tggtttgttt t ctatcaggc    8280 tttgtttttt ctatgcataa tatttactca gttaaatttt tgttttgaca a actttctgt    8340 gagccaagct tgtggacgga gatgaaaaga cgagcagctg cctttgagaa a ctcagactc    8400 tgggccagcc catctgggtg ccagctttca ctgctccacc cactagctgg g tgaccctgg    8460 gcccgtgact ttacccctct gttctttggt gttctcatat gtaaaatgag g ataataata    8520 gtaaccagtt catagagtgg ttgtcagaca gaatgattaa tgtacgtaaa g ctttcagga    8580 tggtgccagc aagatgcaca ggagtgtttg gtaggaggat gacgaagctt a ccgtctggc    8640 aggaggggca gttgtaacat gctgggctgt gatagtacag atgtgtttaa g tgagggag    8700 agcccagagc aaggagagag aacctggcat ctggtgatgg tgtatcaaga a catttagg    8760 ccagacacgt tgactcacac ctgtaatccc agcactttga gaggctgagg c aggcagatc    8820 gcttgaaccc gggcgttcga ccagcctg agcaacgtgg taagaccctg t ctttataat    8880 ttttttttt tttttctga gacggagtct tcactctgtc acctaggctg g agtgcggtg    8940 gtgctatctt ggctcactgc aacctccacc tcccgggctc aagtgattct c ctgcctcag    9000 tctcccaagt agctgggatt ataggtgccc accaccatgc ccagctaatt t ttttatatt    9060 tttagtagag acggagtttc accatgttgg tcaggctggt ctcaaattcc t gacctcaag    9120 tgatctgccc tcctcagcct cccagagtgc tgggattacg ggcatgagcc a ccatgcctg    9180 gcctctataa aaattgtttg gaagaaatta cctaggcctg tgatacaca c ctgtagtcc    9240 tagctactca ggaggctgag gtggaaggag gtagaggctg cagtgagcca t gattgagcc    9300 actgtactcc agcctgggca acagagccag acctgtttc aaaacaacaa c aacaaaaac    9360 atttttaagg aggaggctga gaaccacgag aaccaagctt ggatttgaag a aggatcagg    9420
```

-continued

```
gctttctcag acagaaaagg agaggaagaa cattccagat agacatcatt g agagatggc      9480 actgagcctt gtaatgggac actgcgaact tttcttcagt tgttatgatc t tttttttt       9540 ttttttgag acggagtttc gctcttgttg cccaggctgg agtgcaatgg c gccatctca       9600 gctcaccgca acctccgcct cccaggttca agcgattctt ctgcctcagc c tcccaagta     9660 gctgggatta caggcatgcg ccaccatgcc tggctaattt tttgtatttt t agtagagac     9720 ggggtttctc catgttggtc aggctggtct caaactcctg acctcaggtg a tccgcccga    9780 gtcggcctcc caaagtgctg ggattacagg cgtgaaccac cgtgccttgt t ggtataatt    9840 attagtattg atcttttttc cttttcatgt gcctcttagt gggccccttg c ttttgtctt    9900 ccttctgtcc ccagggttga tcctgtgctc agcacatagg ccagggaaga a tgtggctgt   9960 gacccagtgt ccactcagat gtcctctctc ccccagggca cccatactct g tccttagtg  10020 tcttttgtct ggtgacatct tggcacagag gcagagggcg gcctccgtct g attggcgcc  10080 tggctttggt gacagtacct taggaaggca gtgtattttc tgggaaccta g gaaataaca 10140 aggtatctaa ttccatcatc aacactgggg acaatttcca tggcagaaac t atgactctg 10200 aatatgcagc gtaaagttac cacccagaca ctgctgctcc tgagtctcga a tggcatctt  10260 ctgcaggggc tcccccacct gcccctgcag aaggtgcagt tcgttcattt c caaggagct 10320 tgcttttgtg tgctgtctct cggagctctt tgggaaacct gtggtagcag g aaacaaagg 10380 atttagacca atgccgatga tccccttgct ccgatagagt gtgacatgat g ctggtcacc 10440 ttttggtatc taggagggg gacattgatt ttgtttgcgg aagtgaaatg a tccatgctg   10500 gcctcttttt ttttttttt ttttgagaca gagtcaccct atcgcccagg c tggagtgca    10560 gtggcgcgat ctcagctcac tgcaacctct gcctcccggg ttcaagtgat t ctcctgcct  10620 cagcttcccg ggcagctggg actacaggcg cctgccacca catctggcta a tttttgtat 10680 ttttagtaga ggcagggttt cgccatgttg gccaggctgg tctcgaattt c tgacctcaa 10740 atgatccgcc cgcctcagcc tctcgaagtg ctgggattac atgcctgagc c actgtgtct  10800 ggtccatact agcctctttg agtgctgaaa ggttatctct gtaacttatt t agtgagaac 10860 cctccatttg cccagggcat tactgcctat aatgtatgtt cacatgtgct a tctcctttg  10920 gtcaatacca cacactacag gtgaggaaac tgagtctctg ctgggacact g ggtcaggaa 10980 gcaggcagtt aagtcacct gtgcacagtg gcagcacagg gggacagcct t ctaggtagc  11040 cagcctggcc tgagggttct gtcacttta cctcccactc agtgttgttt c tctttcttt   11100 cccctccttt taagatccct ccaggcccag gatctgggga caacgctggt g gggagtgat  11160 ctgggtgtct gtgcaggaaa ccgctgcact gggtgagatg gcatgggag a ctgtgcctg    11220 gctgaccaga gacctcgttt cttccagac agaggggaa gacggtgggg c ctccccacc    11280 tgccccgcag aagatgcagt tctttggccg cctggtcaat accttcagtg g cgtcaccaa  11340 cttgttctct aacccattcc gggtgaagga ggtggctgtg gccgactaca c ctcgagtga  11400 ccgagttcgg gaggaagggc agctgattct gttccagaac actcccaacc g cacctggga 11460 ctgcgtcctg gtcaaccccca ggaactcaca gagtggattc cggtgggtga t gctcagcgg 11520 gaacatactt ctctcctttc actccccac gtctcggatt ggaggtctta t tggccgaga  11580 agcagtttct ttgagtctct gtctgagggg tctggagagg ggtgggagag a ggggagact 11640 gtactcttgg accagaggga agggcttccg agactccaca cttctggccc a tcagtgtcc  11700 cagcacgagg ctgaggatgg aagcctgggt tgtttctggc ctggaggctc g acctatatg  11760
```

-continued

```
gacaaaggga agaaggaagg acagggagac tgagagtgtc cacatcagat a aggcccatg    11820 gggagaacct ttagccctgg ctctttattt ttggttttgg tttttgtttt t tgagacagt    11880 cttgctctgt tgcccaggct ggagtgcagt ggcgcaatct cggctcactg c aacctctgc    11940 ctcccaggtt caagcgattc tcctgcctca gcctcctgag tagctgggat t acaggcacc    12000 caccaccacg cccagctgat ttttgtattt ttagcagaga cggggtttca t catattggc    12060 caggctggtc tcaaactcct gacctcaggt gatctgccca ccttggcctc c caaagtgct    12120 gggattgcag gcgtgagcca ctgcacctgg cctagccctg gctctttaag g gcatggccg    12180 ttctcatagg ggctgcccag ggtttgctta ggaaggctgg acagagctgt t gcctcttgg    12240 ggcatgctgg gactcccctg ggcctgaaga gaaggctcaa aagccaggac a ggcctgagg    12300 gaaccgggcc aacggcagag ctggttggga aaaggggaga agcagccaag g ttccaaatg    12360 caggccccag cagtgcttgg cagactggca tctagttggg ctcagacaga t atccctgtt    12420 tccgctcacc tatccatctg gctgtcctgt cagccatcca ttcaacatgc a ccaagcacc    12480 tccagtgtct ccagagtcct gggcttcggg ccagtcctgg ctggcctgtg a gatgacaaa    12540 catgtcctgt gtctttaagg aacgtacagt ctggtggggg aggtccggtg c aaacaggcg    12600 tcatagcacc ccttgaggag tgctgtgaca gagggagagc ctaggaaaca g tgtggatca    12660 caaggaggtg attgagagct actctgcgtc tggaagagtg aggaggagcc t gtgtggcag    12720 aacaaaatgg ataaggtcgt tccagccgtg cagaagtgtg gaggtgtgag c ctgcaggca    12780 ggtggctctg gttggatccc agtgcatgc agggcttttgg tgagagtgag g ctgaaggaa    12840 gcagctgggg actcattctg actaaagagg catggcagga ggggtctctg a aagtgtcag    12900 gctgggggcc aggggctgcc accaacagaa gagcaaggca ggtatcaggg c cccatccaa    12960 tcaggtgaga attcagagcc tggctccaca aggaacctga ggcagaggca c ccacagcag    13020 gtgcttgggc taaatgcagc tcagtggcca gtgcaggcac cagttttaat a cagtggggc    13080 cattccagat tctgagtgca gatggggctg agcagaccgc cttccagctg g actcgatca    13140 ggactgaccc tggacggggc aggcttgcac ttgtagcttc agagctccac t gcaggcaca    13200 gctgaccagg gcagcgggtc cactccttgg agagctggac agccccactt t gaggtaca    13260 cggccctggg gataccacta atctccacgt accaataatc accaagttct g tcagttgta    13320 aaatcccttg acaggattcc agatttgtct cagccagctt aagccccagt g tgggcagac    13380 ctccatccca ggaggattta gtcctttgtc agcagcttct tagctacacg t aagctattc    13440 tgtggtactt tatagtttac aggattttttt gttttctttt tttttttttt t tgagacaga    13500 gtctcgctct gtcacccagg ctggagtaca gtgacgcgat ctcggcttac t gcaagctcc    13560 gcctcccagg ttcacgccat tctcctgcct cagcctccca agtagctggg a ctacaggca    13620 cccgccacca cgcctggcta atattttgta tttttagtag agatgggggtt t caccatgtt    13680 agccaggatg gtctcaatct cctgacctcg tgatccgcct gcctcggcct c ccaaagtgc    13740 tgggattaca attttacagg atgttttttaa gtatgttggg ttagcacatt c tctgccaat    13800 ccgtggaggt gggcaaggaa ggcagtattc cattttatgc atgagaaaat a gccttggga    13860 tgataagtga ttcatcccac ttatacacag gaagcagtga agaaacagaa t cagtgtctt    13920 ctggttccca attcatttct ctgtgctgct gtgttgtttc catgtatgta t gtatgtatt    13980 tatttttttg agacgttaag tcttgctctg ttgcccaggc tggagtgcag t ggcatgatc    14040 ttggcttaca gcaacctctg cctcctgggt tcaagctatt cttctgcctc a gcctcccga    14100 gtagctgaga ctacaggtgc gtgccaccat acctggctaa ttttttgtgtt t tttagtaga    14160
```

```
gacagggttt cactgtgtta gccaggatgg tcttgaactc ctgacctcgt g atctgcctg   14220 ccttggcctc ccaaagtgct gggattacag gcatgagtca ccatgcccgg c tttgtttgt   14280 cttatttcta aattttattg atttatttat tttcacagtc atagctctgg a gtctttttt   14340 atcttctccc ctctaacctg ctcccacccg aacctttcca tttcagcaga t agcatcatt   14400 gcaacgggct gtgccagatc cagccatcac atccacctttt ccagcaaag g gagggtgga   14460 agggcaggat gcagaaggtc aatctccccc tcctcaggga catttcatgg a agttgcacg   14520 cattggccag aacccggtca catggccaca gctaactgca aaggatgctg g gaagtgttg   14580 cctgtgttgc agacagccac gtgccagtcg aaaatcagag gttctttctc c ctccgtctt   14640 gctgctggct cgcttctcca gaccacagtc attgtgcacg tgtctcctgc t gctccggct   14700 gtggcctgca ctcctctcat cctcttccaa gctgctgtca cagcgctgtt t ccagagggc   14760 aaatctgatt ggtcactccc ctgctttact ccccaagggc ttcctgtttt c ttttatttt   14820 tattttattt ttcatttttt gagatggagt ctcgctctgt cgctcaggct g gagtgcagt   14880 ggcacaatgt cagctcactg caagatctgc ctcctgggtt catgccattc t cctgcctca   14940 gcctcccaag tagctgggac tacaggcgcc cgccaccacg cccagttaat t tttttgta    15000 tttttagtag agacggggtt tcaccatcta ctcttagcca ggatggtctc g atctcctga   15060 ccttgtgatc tgcccgcctc agcctcccaa agtgctggga ttacaggagt g agccaccgc   15120 gcccggccag cttcctgttt tcttaacaca tcaggtgctt aatgacttaa a agggcccag   15180 tgtgatcaag tttctgcctc tgtgttctca gctcatgccg ccttgtgctc c tggcctttg   15240 cccaggctct tgctgtggcc tggaatactc cctttctttt gcctgccttc c ttcctcttg   15300 ccctcccctg acctgcaggc tggattagga gtttctgctg ggcatcccat g gcacccgtc   15360 cctgcactgg ggatcctgct ttcctggtag gccacagacc ttgtgagggg a gggactgtg   15420 tctgttgggt tcatgacagt gtgcccagcc cccagcaggt gcctggcgta g atcaggttt   15480 gtggaacaaa tgaatgtgat atattaattt agctttagag tattcattga g ggctgctgt   15540 gtgccaggcc ctctgtgcca cctgggtgga gggtggagga ctgttgcatt g agggcagtt   15600 gaaggagtga gctgggaagt gggaggtgga ggatggggac tgggatgcag g gtttgaggt   15660 tatcagggt cccagaagca gtaatgccaa ggcctaggct gtgacctgga g tgagggctg    15720 cgatggggtg gggtggggtc gaggctgtgg aggagggtca tcagggcact g ctggagccc   15780 tggggttctc cagggccggg ggtggtcatt gcagtgttct cccagctcct c tcaacaccc   15840 tgcggtctgt ggagagcagg cctggtgcac tggacttgcc tctggccagg g ctgagtttc   15900 tgccttctaa acgatcttcc tcctgtgttg ccctagaggc ctctggactg t cctgagtac   15960 ttgacgcgtg ttagagtgag catgggctgc tagccttccg ctccaggtgg a ggagtttct   16020 gttgttcttt tgctgctgtt gctgcagtga gctgccaggc tgagcttctg a tggacctg    16080 ggggatggaa ttaggagctt ctgaattctt gggttgtata acctaaggcc g gagagtccc   16140 acagcactgc tgctgggcgg agagactgga ccctgctgat acagacagcg a cagcagcag   16200 gagcatctgc agtttcccag caggtcctgc atgcctgggc ttggcactag t ctaagtagt   16260 aactcatgtt atcctcacga cagtcccacg aggtgggtc attactgacc t cctattaca   16320 gatgaggaaa cagaggcttg cagaatttga gatcacacag ctggtcagcg t agcgattat   16380 tcagaccctg tcacctggct ccagaaccca ctcgtttacc tttcttacat c agggctgct   16440 ttgtagtgtg gcgagctgag tggagctcca cccgcctggg ctgatcctgg c ccttcctgc   16500
```

-continued

| | | | | |
|---|---|---|---|---|
| ctgacctatg | gtgcgggggc | cctggctctc | cccgtgtgag | cccccagggg t cacttgtaa 16560 |
| tatgcctgtg | tacactatga | tagcatagat | acttctgttc | ctggtacaga t taatcattt 16620 |
| acggctggca | ttgacttgta | acagatgaca | tttgatgaaa | tcaaccagcc t ctcactggt 16680 |
| atctcagcag | aaacagggct | gtacctccca | ggcatcctgg | aaggatgat a gaagtgtgt 16740 |
| gatctgtgct | tccctaccgg | gagctgactt | ttgaggctct | ctggactggg a ctttgccat 16800 |
| aaaactgctt | atcagaaacc | tcagataagt | ggagtgccct | gtgtcctggc c acgtactct 16860 |
| gggccagct | cctccatcca | ttcagtcctc | ccacatccca | tcttcaccaa g cagagtgga 16920 |
| aagcggcagg | tctctgcgag | aaaaggaggc | tctgtaccca | gccttcagtg a gataactttt 16980 |
| agagtggggc | cttgtattcc | ctacacaggc | cttgtccccg | acacggcctc t ttgcccttg 17040 |
| cttctccttc | tgctaagaat | gctccttccc | aactccttgg | ctggacacac g gctcctgct 17100 |
| ctgtgggcct | gtcctgttcc | cactcagagc | ctcagcaccc | ccatgtggc c aagacacag 17160 |
| ccctcttgc | cttaggttgc | cgtgggtctg | tttccacatc | tgtttcccct c cagactgca 17220 |
| gggctcctga | gggacagggc | ctggggccaa | gtctcctctg | cgttcctgat g cctggtggt 17280 |
| gtgccacgct | ctccgtgggt | gcacggtaaa | tatctgccga | gtggctagat g tatccatgg 17340 |
| ttgctgaagg | ccaagtgtgt | tgaccagagg | gcgtgggaaa | ggctccactg g ggtggctgg 17400 |
| ggtagagata | gaccttaagg | ggtccagaag | actccaccag | ctggagggaa a ggccctaca 17460 |
| gagacaaggt | actaggaaag | gcccagagga | cagaggaggg | gccctgtggg g agcctgtgg 17520 |
| gcaggaaggg | cctgtgctgg | gctttgaaac | tggggactca | ggtactgctc t agcgtgagg 17580 |
| gtccttggca | tttttttttgg | tccaggaccc | cctgaggtcc | ctggggaatg a gaacaggct 17640 |
| cacacagcca | ctttcaagag | gtttgcaggt | cccctgagcc | ttagccacag a cccctccca 17700 |
| ccccagcaga | gacacagcag | aggcttctga | gtggaggcca | ggtggcttca g cctggggtt 17760 |
| ctagaaggga | gggaagagac | acaccccgt | gtgtcctcca | gagcctcagc c ttctccctg 17820 |
| aatctcccct | tgcctcctc | actgtaaccc | acacctggct | ctccttgaag g acccgcttg 17880 |
| ccccgcagcc | tcctgagagt | tttctctccc | agtccctctc | ccactgggcc t ggaggtggg 17940 |
| gtagggtcct | ccttgccccc | agccttgaat | cttctgtcac | cctacaatac c acttgctgt 18000 |
| cacccccggtg | ataggtatct | acgagcctgg | ggtgctcccc | cacatcctca a agatgtgag 18060 |
| ccccctgactc | agcgttgcct | ctggttcctg | accctccaca | ttcacatgac c acgcgctgg 18120 |
| cctttatcat | cgccagtgac | agcagctctc | ccgtaaatac | aagtttcaag c accccactt 18180 |
| tccagtctct | gccttctgtc | tttccagttc | attccctcta | gtcctccacc c acacagtgc 18240 |
| ttttccccat | tgacagggaa | ttgctcctgg | ccgcttttcc | cagccccatc c cgttcatgt 18300 |
| gccttgcttt | gtacccagca | tggactccat | ggcctgtcat | tgtcactcct t cacctatac 18360 |
| ttcctgcctc | cttgcttctc | tctctcttcg | tcatcctggc | atcaccaccc c agaactgct 18420 |
| tggtttcagt | tctccaccat | ggctagggga | acatacctttt | ttgctgactg c tctcacttt 18480 |
| cttttttttt | tttttttcttt | tttttttttt | tgacacagag | tctcgctctg t tgcccaggc 18540 |
| tggagtgcag | tggcacactc | tcagctcact | gcaacctcca | cctccggggt t caagcagtt 18600 |
| ctctctgcct | cagcctcctg | agtagctggt | attataggca | cccgccacca c acccggcta 18660 |
| attttttgtat | tttttttagt | acagacaggg | ttttgccatg | gtggccaggc t ggtcttgaa 18720 |
| ctcctgacct | caggtgatat | gcctgccttg | gcctcccaaa | gtgctgggat t acaggcatg 18780 |
| aaccaccctg | cccggcccta | ttgctctcac | tttgaaatca | cgacatgagc c acagtgagc 18840 |
| ctatgatgtg | gtttgacgtc | tttctgcatt | tctctgttca | ccctctcccc a gaaggcatg 18900 |

```
cctccttccc tccccctcagc ctgcagcccc ttcccctcca cgcttactct c agctgatag  18960 ccctgctgct gtctcgctga gaaaatagaa atagccagag gagaattccc t ctaccccat  19020 gcacacacct ctgtccccgc ctactccaca ttccctgttg tcagcaccga t gtgtttagc  19080 tgagggtggt cccccccattc aaggccatca tctcctgtca tctacttctt g acaccattt  19140 gaacaattat ctcccctctt tcctacataa cactttcccc ttttctacta t atatttttt  19200 gctatggatt gaaagtatcc ccccgaaatc atatgttgaa gccccaatcc c tcgtgtgat  19260 ggtattagga ggtagagcac tatgggggtg attaggtcat gaggatggag c cctcatgaa  19320 tgggattagt gcccttagac gaagaggcaa gaaagagatg atctgtctct g ccatgtgag  19380 ggcacaacga gaagatagcc atctgcaaac caggaagtga accctcatca g gaactctat  19440 cagccagcac cttgatcata gacttcctag cctctagaac tgtgagaaat a aaggttgtt  19500 taagcctccc agtctgtagt tttctgttat aatgtcctga cctaagttat t ttccatcgc  19560 tatacaatgg gttattttt tctttaaaaa aaaattattt cttgactcta c ttttttcctc  19620 cagagactgc ttatattcca ctgtcttcat tcttctcctc ctgttttctc t ctttaaact  19680 tttcaaaaat agcaaaatat aacacatata gagaaaatga tatacagctc a gtgatttat  19740 cacaaacacc tgtgtaacca ccactcgaat ctagagatag gacattacag c accccagaa  19800 gccctccttt tgtcccctct tcccaaagaa gggtaaccaa taacttgcct t ttatgataa  19860 aggctttttt tttttgagat ggagtctcac tgtgttgccc aggttggagt g cggtggcgc  19920 aatctctgct tactgcaagc tctgcctcct gggttcacgc cattctcctg c ctcagcctc  19980 ctgagtagct gggactacag gtgcccgcca ccacgcccgg ctaattttt g tattttagt  20040 agagacgagg tttcaccgtg ttagccagga tggtcttgat ctcctgacct c gtgatccac  20100 ctgcctcagc ctcccaaagt gctgggatta caggcgtgag ccaccgcccc c ggccaagat  20160 aaaggctttt ctatctggct tctttgttag cattttgttg gcgagattga t acgttttgt  20220 gtgcagctgt ctgtcatttt cattgcaata gaattccatt gtctactata t cacagttac  20280 tcattctact actgatgaaa atttgggtta tttctagttt ttttggtgca t acatgcata  20340 catttctggt agacatacct agaagtgaac tggctgcatt atgggccata a cttgtcttc  20400 aacgttagta aataataccg cccgtctgtt ttccaagcag cagtaaatgg c actttctgt  20460 tacttcatat cttctgttac ttggtactgt caggtttttaa aatttttagtc a ttctgtcgg  20520 gtgtctagta gtatgttatt gtggttttat tttgcatttg cctgattgca a atgaagttg  20580 agcactttt gatacagtga ttaaccattt ggatatcctc ttcagtgaag t atcagctca  20640 attctcttga ctatttaaaa aataaagttg tttatctttt tcttacagag t tttaggagg  20700 agttttttgg tacatgtgca gtccaaatac acaccttttg tcagtgatac g tgttcagct  20760 gcacacacgg tgttttgcct ttttattctt ttaatggtat ctattgataa a catgagttc  20820 ttagttttaa tgaagtcaaa tttgttcatc ttctttacgg tgtactttt g tgtcttgtt  20880 taaggaagtc cttctctatc ttaaagcttt gagaagcatt ccttctttct c ctattttct  20940 aaaaattgtt gaagatctcc ttccttcctt ccttccttcc ttccttcctt c ctttcatct  21000 atctctctct cacccaggcc aaacttcagt ggcatgatca tggctcactg c agcctcaac  21060 ttcccaggct caagtgatcc tcctgcctca gcctcctgag tagccaggac t acaggcacg  21120 caccaccata cctggctaat tttaaaaatt ttttgtagag acacggtctc a tcaagttac  21180 ccaggctggt cttgaactcc tgggctcaaa caatcctccc acctcagcct c ccaaagtgc  21240
```

```
tgggattaca ggcatgagtc acatgtctag cctgtattct ttctttctta a atgtttgga   21300 agaattcatg ggtaaaacca tgtgaccctg gagtttattt gtgggaagct t ttaaaacat   21360 ggattcgatt tctttaacaa atataggact atgagatttt catctcatgt c ggtttgggt   21420 atgttgtgtt ttcaaggaat ttttctattt tatcgaagtt gtcaaatttg t ctgcaggtc   21480 cccttatttc cttttaatg tatggaggat ctgaagggat ggtactttgt g ttgtctcta   21540 tttcttgttt ggttttgcta gtgatttgcc aatttaaaaa atctttccaa a gaaccaact   21600 tttggctttg tttatttttt gaaaacctga gtagctggga ttacaggcgc c caccaccac   21660 acccggctaa tttttttatt tttagtagag gtggggtttc accatattgg c caggctggt   21720 ctcgaactcc tgacctcaga tgatccaccc gcctcggcct cccaaagtgc t gggattaca   21780 agtgtgagcc agtgtgcctg gcaagccgct ttttaaatgg caccaatccc a ttcatgagg   21840 gcagagccct gatgatcgaa ttacctccta atggccccat tcttaatac t atcacactg   21900 agaattaagt tttaacataa gaattttagg aagacacaaa cattcagacc a tgaacata   21960 tataaaacag ttgtcctacc aactaacaga atacacattc ttttcaagaa c acctatata  22020 aaaattatag acactgacct atgctggcca taaagcaaat atgaacaaat t tcagatacc  22080 tgaagagatt tagactatgt tctccaacta cagtgcaatt aagctagaaa t caatagcaa  22140 aaatgtaact ataaatgagc ccgtatgttt gaattttaag caagatatat g taaattatc  22200 tatggttcaa aaaagaagtc acagtgaaat ttagaaaata tcttgacgtg g cgggttgca  22260 gtggctcacg cctgtaatcc cagcactgtg ggaggccaag gcgggtggat c acctgaggt  22320 aaggagtttg agaccagcct ggccaacatg gtgaaaccct gtctctacta a aaatacaaa  22380 acattagcca ggcgtggtgg tgggcacctg tggtcacagc tacttgggag g ctgaagcgg  22440 gagaatcact tgaacccggg aggcagaggt tgcagtgagc cgagattgca c cactgcact  22500 ccagcctggg caacatgagt gaaacttcat ctcaaaaaaa aaaaaaaag a aaagaaaaa  22560 gaaaatatct tgacccaatg atgatgcaaa tactacgtat caaacttgta g gatgaactt  22620 ccacttctgg ccatgacaga ggagcctgta tcagactagc cttcctattt a tatatttat  22680 ttttgagatg gggtgtcgct ctgttgccca ggctggagtg cggtggtgca a tctcagctc  22740 actgcaacct ccacctcctg agttcaagta attctcctgt cccagccttc c aagtagctg  22800 gaattacagg cgcccaccac cacacccagc tagttttttta tattttagt a gagacgggg  22860 tttcaccatg ttggccaggc tggtctcgac acctgacctc aggtgatcca c ctgccctg  22920 cctcccaaag tgccgggatt acaggtgtga gccactgcgc ctggccgtga g tgacctttt  22980 taatgtgttg ttgaatttga tttgctggta ttttgttgag aagttttgca t caatatcca  23040 tcagggatac tggcctgtag ttttcttttt ttatatgtct ttgtctggtt t tggtgtcag  23100 ggcaatactg gcctcataga atgagtttgg aagttttctc tcctctgttt t tcataatag  23160 tttgagtagg gttggtatta gttttgttt aaatgtttgg taaaattaag c agtgaagcc  23220 actgggtccc aggcttttct ttgctgggag acttttcatt acagctttga t ctcattact  23280 tgttattggt ctatttaggt tttggatttc ttcacggttc catcttggta g gttgtgtat  23340 gcctaggaat ttatccattt cttctagggt tttcaattta ttggcatata a ttgttcaca  23400 gtaacctcta ataatccttt gagtttctgt gatattggtt gtaatatctc t tttgtcatt  23460 tctgattttt ttgtttgggt tttctctctt tttttgttag tctagttaaa g atttattga  23520 ttttgtttat cttttcaaaa aactttattt tgttgatctt ttgtattgtt t tgtttcaat  23580 ttcatttatt tctgctatga tctttattat ttcttttctt ctactaattt t gggtttggt  23640
```

-continued

```
ttgctctttt ctagttcttt aagagacatc attagattat tttgaagtttt t tctacttac   23700
ttgatgtagg tgcttatagg tacaactttc ctcttagtac ttctttccct g tatctcaca    23760
ggttttgata tgttgtgttt ccattatcat ttgtttcagg atgttttttaa a tttccttct   23820
taatttcttc attgaccatt caagagcata ttatttcatt tccatgtgtt c gtatggtgt    23880
gcaaaatacc ttgtttttga tttgtagttt tatttcattg tgatcacaga a gatacttga    23940
tatgatttca aatttaaaaa gtaatttggc tgggagaagt ggctcatgct t gtaatccca    24000
gcgctttggg aggccgaggc aggcagatca cgaggtcagg agatcgagac c atcctggct    24060
aacacagtga aacccccgtct ctactaaaaa tacaaaaaat tagccaggca t ggtggcagg   24120
tgcctgtagt cccagctact caggaggctg aggcaggaga atggtgtgaa c ccgggaggc    24180
agagctggta gtgagccgag atcgcgccgc tgcactccag cctgggtgac a gagcaagac    24240
tctgtctcaa aaaaaaaata ataacaataa taataattta agacttgttt t gtggcctac    24300
catatggtct atccttgaga atgatccata tgctgaggag aagaatgtgt a ttctgcagc    24360
cgttggatga aatgttctgt aaatatctaa taggttcatc tgatctatac t gcagactaa    24420
ggctggtgtt tctttgttga ttttctgtct ggatgaactg tctaatgctg a aagtggagt    24480
attgaagtct ccagctatta ttgtattgag gtctatctct ctctttagct c taagaatac    24540
ttcctttata tatctgggtg ttccagtgtt gagtgcatat gtatttaaaa t tgttacatt    24600
atcttgctga attgaccctt ttatataatg accttctttg tctcttttta t agtttttgt    24660
cttgaagtct gttttgcctc atagaatagc atagctattc ctgctcttat t tggtttcca    24720
tttgcatgga atatcttct ccatcccttt agtttcagtc tatgtgtgtc t ttacaggta     24780
aagtgtgttt catgtaggca acagatcact gggtcttgtt tttctatccg t tctgccact   24840
ctgtgtcttt tgattggaga gtttagtcca tttatgttca atgttattac t gacaagtaa    24900
ggacttactc ctgccacttt attaattatt ttcttgttgc tttgtgatct t ctttcttc     24960
cttcctgttc tccttttagt gaaggtgatt ttctctggtg gtatgtttta a tttccttgct  25020
ttttattttt ttgtgtgtat ctgctgtatg ttttttgatt tgaggttaac a tgaggcttg    25080
caaataatat cttataaacct aatattttaa actgatgaca ccttaacact g attgcataa   25140
acagacaaac aagcaaagag aaaactaata aaaactctac atttttaactt t gtcccccca   25200
cttttttaact tattgtactg tttatgtctg aaaagttgta gttattattt t tgattggtt   25260
cctcttttag tctttctact caagatatga gtggtctaca tatgacagtg t tataatatt   25320
ctatatgttt ctgtgtactt gctattacca ttaagtctg tactttcaag t gatttctta    25380
ttgctcatta atgtccttt ctttcagatt gaaaactcc ctttagcatt t agcagtatg     25440
tgaactgcat ttttcaagtc cagaatttct gcttgattct ttttttttttt t ttgagatgg  25500
agtcttgctc tgtcgcccag gctggagtgc agtggcgcga tttccgctca c tgcaagctc   25560
tgcctcccgg gttcacacca ttcttctgcc tcagcctccc gagtagctgg g attacaggc   25620
gcccgccacc acgcctggct aattttttgt attttttagta gagatgggat t tcaccatgt  25680
tagccaggat agtctcgatc tcctgacctt gtgatccgcc tgccttggcc t tccgaagtg   25740
ctgggattac aggcgtgagc cactgtgccc agcctgcttg attcttttaa a ttatttcaa   25800
tctctttgct aagtttatct gttaggattc tgaattcctt ctctgtgtta g cttgaattt   25860
cactgagttc cctcaaaaca gctattttga attctctgtc tgaaaggtca c atatctctg   25920
tctctccaga attggccact ggtaccttaa ttagttcatt tggtgaggtc a tgttttcct   25980
```

```
gtatggtctt gatgcttgtg atgttcgtca gtgtctgggc attgaagtta g gtatttatt    26040 gtagtctttg cagtctgggc ttgtttgtat ctgttcttct taggaagact t tccaggtaa    26100 taaaagggac ttgggtattg tgatctaagt ttttggtcac tgcagccata t ctgcattag    26160 ggggcacccc aagcctacta atactatggc tcttgcagac tcgtaaaggt a ccacttggg    26220 tggtcttgga taagatctgg aagaattctc tggattacca ggcagaggct c ttgttctct    26280 tcccttactt tctcccctaa aagtggagtc tctctctctg tgctgggccg c ctggagcta    26340 ggagaggggt gacacaggca cctctgtggc cactatcact aggactatgc t ggctcagac    26400 ctgaagccag cacagcactg ggtctcaccc aaggcctaca gtctccactg c ctggctact    26460 gcctacgttt gcttaaggca ctagggctct acagtcagca ggtggtgaag c cagtgagat    26520 tatgtccttc ccttcaaggc agcaagttcc ccctaccccc atcctgggaa g gtccttaga    26580 tgccatctgg gaggcagggc ctgcagtcag aaaccttagt aatctcccca g tgctctatt    26640 ctattacagc ctggctgata cccaagccat aaggcaaagt ccttcctgct c ttccctccc    26700 ctttccacaa gcagagaagt ctctctccat ggccaccact gccccagccc t gtggcagtg    26760 ctgccaggcc actgccaacg ttcattcagg gcctaagggc tcttgaagca a ctgaacact    26820 gccaggcctg ggactctccc tttagggtag tgggctcccc tctgacccag g gcaggtcca    26880 gaactgccac cccacagcca acacttagaa tctgggaccc caagagccct c ttggtgctc    26940 tgccacactg tagctgagct ggtacctagg ctgattttg cttttatga a ggtactttt    27000 ttgtgtgtat agttcaattt ggttttcctc cagggaggac aattggtgga g gtttctatt    27060 tgggcatctt ttttttttt ttttgagacg gagttttgct ctttcaccca g gctggagtg    27120 cagtggcgcg atctcggctc actgcaacct ctgcctcctg ggttcaagcg a ttctccagc    27180 ctcagcctcc ccagtagctg ggattacagg tgcctgccac catgcttggc t acttttttt    27240 ttcaattaaa aagtaaactt taatgtcgaa aatgcaaact tggggaaggc a gaaagatca    27300 cacacaaggc tgtcgcttca cacttggaag gttgcacggc ggccaggaga g gcactcctc    27360 acttcccaga cagggcgggg gccgggcaga ggcgctcctc acttgccaga c ggggcggcg    27420 gccacatgcc tggctaattt ttgtattttt agtagggacg gggattctcc g tgttggcca    27480 ggctggtctc aaactcctga cttcaggtga tccacgcacc tcggcctccc a aagtgctgg    27540 gattacaggc atgagccacc gcgcccagcc ctatttggcc atcttgcttt g cctccacct    27600 tcatttgata acagaacacc cccatgtaac caccaccaca atcaagatat a agacatttc    27660 tgttattctc caaatttcct tcaccctcct ttatagtcca tggcacccac c ccatccctg    27720 ggcaacacct atgtgcttcc ttttttttt tccccgcagg aggacgtctt c ctataccta    27780 tgtgcattcc atcactgctg ctttaatca tatagcgtgt agtcttatga g tctgacttt    27840 ttcacttagc ataatgcttt tgcaatttgt gattgagcgt tttcatatga t tctgttttt    27900 tctgtctctt agcttggaag ttatacactt tttagtagta actgttggga g atcgttctc    27960 caagagtctc tctcatattt ccatacatcc tgctagcaga gacattgact a cctgttttt    28020 gtctgtttag tgttgctata aaggaatacc taagtctgag tattatacat g aaaagagg    28080 ttttatttgt ctcatggctc ctcaggccat acaagaaaca tggtgccagc a tcttaccag    28140 tgtcacatgg caagaaagga agtgaggaag agaaaataag ttgttaactg g ttgttaaaa    28200 agtgccaggc acgggccagg cacagtggct cgtgcctgta atcccagcac t ttgggtggc    28260 caaggcgagt ggatcacctg aggtcgggag ttttgagacc agcctgacca a catggagaa    28320 accctgtctc tactaaaaaa aatacaaaaa aattagctgg gcatggtggt g catgcctgt    28380
```

```
aatcctagct actcgggagg ctgaggcagg agaatttctt gaatccagga g gtggaggtt    28440 gcagtgagcc aagatcacct gggcgacaag agcgaaactc tgtctcaaag a aaaaaaaag   28500 tgccaggctc tttttaacaa ccagttctta caggaactaa tagagtgaaa a ctcactcac   28560 ccccacccca cagggagggc attcattcat gagggatcca ccctatgac c caaacacct    28620 cccattagcc ccccacctcc aacattggaa tcaaaattta acatgaggtt t gggggcag    28680 aaatccaaat tatagcacta cctttgttcc aggctacctt caaggatgt t tatacagca   28740 aacagccttg gaaatagag ttagggtctc cttgtagagc acagggtaag t ttgcttact    28800 tttcagcata atcaagattg tgtcttcttc tggagcaaaa ctttgacaac a acaagcggg   28860 gcaaagtctg aaacctttg cacatcttga cagaacctta gagattacga g atttatctc   28920 tgccttactc aaggtccatt agtatcttcc agaacaataa gttggtctta g aatcctta   28980 gctatgtatt cccttccagg cttcgatgct gtgtgctgtt gttttattta g ttttattt    29040 taacccaac aagacgctat accatcaata cttatttaga tcccccaca t atttaactt    29100 gccatggtgc ttcattcttt catgcctctt taagcatcca tctaggatcg t gttcattcc   29160 acatgaagag aaagcttttg gcccagcacg atggctcaca cctgtaatcc c agcactttg   29220 ggaagcctag gcgggaggat cgcttgagcc caggattttcc agaccagcct g ggctacgtg   29280 gcaaaccct gtctctactg aaaatacaaa aaattagcca ggtgtggtgg t tcacgtccc    29340 tgctactcgg gaggctgagg tgggaggatt acttaaacct gggaggttga g gctgcagtg   29400 agcgttgatt gcaccactgc actccagcgt gggtgacagg agtgagacca t gtctccaaa   29460 aaaaaaaag aaggaaagaa aaagcttttg tatttccttt cgtgtaggtc t gctaatgac    29520 aaagtctctg ggttttttgt ttgactagag aaatgtttta attttaacct t attcttgaa   29580 ggttttgttt ttgttttcat tttgttttgt gtgctaagta cagaattctc a ttggcattt   29640 atttatttag agacagagtc ttgctctgtg gcccaggcta gagtacagtg g cacgatctc   29700 cgcctcccag gttcaagcga ttctcctccc tcaacctcct gagtagctgg g ctacaggc    29760 atgcaccact acacctgact aatttttgta tttttagtag agacggggtt t caccgtgtt   29820 gcccaggctg atctcaaact cctgagctca agtgatttgc ctgccttggc c tcccaaagt   29880 gctgggatta taggcatgag ccgccgtgcc tggccagcat ttattttctt t tcagctctt   29940 taaggaagtc attccattat ctctgggttc cattgttgag aagccagctg t cattctaat   30000 ggttgcccttt tgaagataac ttttttccct ctgctatttt aaatatttcc t ccttgtatt   30060 ttatttttcaa caggtgtaat gtggcacata tatcagcaat tgttatgtta c atacaatac   30120 atattgtgca acatatgtat cattatcagt tattgctgtg taacaaacta c tccagaaca   30180 cagtggctta taaaaggaat catttattta gtccttaaat ctgcaatttg a gcagagctc   30240 agtgggaaag cctcagcttt actttatatg gcaccatata aggtaactcg c aactggcaa   30300 gttggtgctg gctgttggct ggtagttcat tcagggctca gggcccagga c caagagtcg   30360 tcaccatggc ttgcttcagc ctccttgagg catgatggct gggtcccaag a gaagagaaa   30420 tagaaacttc cagtctctta aggcattggt ctggaagctg ggacggcatc a cttttgcca   30480 tattctgttg gtaacgcagt tacatcgcca gattaaaggg taaagagata c aaattccca   30540 ctgctcagtg caaggaatat cagtgatttt aggggggccct gttttaaaac c cctacaagg   30600 tgctaagcgt ggatttctgg ggctttcttg ttttttgttt tttctatgt g tttttttttt   30660 ttttttttgg tggtggggtc agggagggct tatagggtat gttaaatcag c agaataatt   30720
```

-continued

```
ttatttattt atttggagat ggagtttcac tcttttgcct aagctggagt g aagtagcgt   30780 gatcagagat ggagtttcac tcttttgcct aagctggagt gaagtagcgt g atctcggct   30840 cactgcaacc tccgcccgc tggttcaagc aattcccctg ccttagcctc c caagtagct   30900 gggattatag gcacccaccg ccacgcccgg ctaatttta tatttttagt a gacatgggg   30960 tttcgccatg gctagtctgg aattcctgac ctcaggtgat ccacccacct t ggcctccca   31020 aagtggtggg attacaggta tgagccactg tgcctgacct ataatgtttt t taaaaatca   31080 gttttggaaa gtttgcagac attaacttt caaatgtagc ttccatttga t tcttttct    31140 actctgcctc tgatcctcca cttatgtatg tatgctagat cttttattag a tagtctgtg   31200 tctcttatgt actctactat attttgtatt cttctgtctc tccatgcttt a ttctgttta   31260 ctctttcctg attatatttt ttaatttgt aatttccatt tgatgctttt t tgatcattc    31320 aaaactcttc accaaaattc taaatttcct ttttaaccct ctcgaatgtt a tcacagtta   31380 ctttaaagtc tattttggat aacttaaata tttacagtcc cctcacagat a tgtttcttt   31440 tgtatattgt ttctgttggt tttctttcat gtcttatctc cacatatgcc t ggtgagttt   31500 tgattatgtg ttggtcattg tatttgcaag tatgctcgta gaaataatct g gaatggccg   31560 ggcgcagtgg ctcatgcctg taatcccagc actttgggag gctgaggcag g tggatcacg   31620 agatcaggag atcaagacca tcctggctaa catggtgaaa ccccatctct a ctaaaaata   31680 caaaaaatta gctgagcatg gtggcacgtt cctgtaatcc ctgctactcg g gaggctgag   31740 gcaggagaat cacttgaacc aggaggcaga ggttgcagtg agccgagatc a cgccactgc   31800 actccagcct gggtgacaga gcgagactcc gtctcaaaaa aaaaaaaaa a aaaaaaaa    31860 gaaataatct agagcctagt ttgatgtttc cttacaaaga atgaatttat t tttgcttct   31920 cccattgcaa ctaggataac ctcagtctag tttctggaac tgaaatcact t gaggctgaa   31980 ctgtggtctc tgtgagagcg tgtctgtgta tggctcaccc ttattcctag g ctacgtagt   32040 tcttaggac cctaacccaa agtaagagat gttcatcagg gctctcctct t ggcagacgc   32100 ctgggctcca gtccctgtgt cctgagcccc atgaggctgt tactggtgct g ctcgtctgc   32160 ccatcctctc cagtaacagc cacctgaaca ctgcaattcc tgggtttcca t cattccttc   32220 cagcctggtg agtcatcagt gtcttttgag gtatccagtg cctgccagca g atgttttt   32280 aataatttgt ccagcatttc tggctgtcct cagtaggtgg tctgtttcac a ttccctagt   32340 ctgctgttaa tggaaagtgg aagttctgag agagaatcat cgttcccgtc a gcattcaaa   32400 tgcctgatta cactttcccc attcgctatc cttttcttta tttgctcctc a ccacagcaa   32460 aactcctcaa aaatatctat ctttgcaatc ttcagattct cacattgtgt c cttaaaccc   32520 actttaatca ggccttggtt ccctccattc cactaaaagt aatgttgtca a ggtcgtgca   32580 tgcctccgtg atgctaattc cagtgatgag ttttcagttg tcattctctg a catatcggc   32640 aacacttgat gtggagtacc ctgatgttga gaggctggtg agatgaagga a aaacccagc   32700 caagggcaat gaggaatggc ttccttccgc ctcctcctc cctatctttg t tgtggtttt    32760 tgttgtttct gtaacactga ttacgttata gtttatttaa tgtacttcct t attctatgt   32820 ttttacttta gtcattttgt tgatctcctc cataataaca taggctcggg c caagcacag   32880 tggctcacgc ctgtaatccc agcactttgg gagaccaaga tgggtggatc a cttgaggtg   32940 aggagttcga gaccagcctg gccaacatgg cgaaaccctg tgcctactaa a aatacaaaa   33000 attagctggg cgtggtagca gcgcctgta atccagcta ctaggaggc t gaagcagga   33060 gaattgcagg agaatcactt gaacccaggg ggcagaggtt gcagtgagct g agatcgcgc   33120
```

```
cactgcactc cagcctgggt aacagagtga gactctgtct caaaaaaaaa a aaaaaaaaa  33180 aggcttcagg agggcagagc attttatgca attgttcatt aattgacccc t ccatttggc  33240 acagatcaca tgcccagtag ttaactgtta atcaacgcac tctctgtgga a caacaggct  33300 ggtcccgttg agccaacact ctctgggcac tgccttcact agactctggc t ggctgctgc  33360 gcttgtagag gtatgcaaga caaaaccttt tggtatgtta aaagccctgg t cagaacttt  33420 aagtaaccat cactgacata taatggttat ggttttgaaa gtgcttttat a gtggttttt  33480 catctgtcct cacagcacct ctgggaggta ggtaggacag gtacagttag t ctcatgttt  33540 caaatgggc tcagagaggg aaaaggattt cccaagatca cacagcacct t agtagcaaa  33600 acttggactc aacctcaaca cttaaaaatg aacaaagctg gccgggcgca g tggctcatg  33660 cctgtaatcc tagcactttg ggaggccag gcaggcaggt cacctgaggc c aggagttta  33720 agatcagcct ggccaacatg acaaaactct gtctcttcta aaaatacaaa a aattagccg  33780 ggcatggtgg cgggtgcctg taatcccagc tactcaggag gctgaggcag g agaatcact  33840 tgaacctggg agatggaggc tgcagtgagc cgagatcgtg ccattgtact c cagcctggg  33900 caacaagaat gaaactccat ctcaaaaaaa aaaaaagaa aagaaaagaa a agaaaagt  33960 ttccctttt ttaaatatct cattttaatg actgcataat agtttattac a tagttatac  34020 cataatttat ataatatttt gttgctgtac atttaggtta aacaatactt a cttagttcc  34080 tactatgaag aggggccaag tactcgaggc tggagctctc acatgtggca a tgaaattag  34140 aaagtggata tggcagggct gtggtaaaat aaaatataaa aataataaat g atattacca  34200 aagaaaagga aagtttttca aaataaagga aaatctagac aagcatagtg g ctcacacct  34260 gtaatcccag tacttttgga ggctgaggca ggaggaacac ttgaggccag g agttcaaga  34320 ccagcctggg caacatagca agaccccctg tcaacaaaaa taaaaaaaaa t taggccagg  34380 cacagtggct cacggtggct agtgcctgaa atcctagcac tttgagaggc t gagggggt  34440 ggattgcctg agctcaggag ttcgagacca gcctgggcaa catggccaaa c ccatctct  34500 actaaaaaca caaaaaatta gccaggtgtg gcagcacacg cctttaatcc c agctactct  34560 ggagactgag gtaggagaat tgcttgaacc cgggaggtga aggtcgcagt g aggtgagat  34620 tacaacactg cactccagcc tgggtgacaa aatgagactc tatctcaaaa a aaaaaaaaa  34680 ttagctgggc atggtggtgc atgcctgtaa tcccagctac tcaggaacta a ggtaggagg  34740 atcccttcag cccaggaatt cgaagatgca gtgagtcatg atcacaccac c gcaccccag  34800 cctgggttac agagcaagac cttgtctcta aaaacaaag aaagtctaac c taaacgcca  34860 ttatgtcatt tacatgtgta tagggtgtg tgtgtgtgtg tgtgtgtgtg t gtgtgtgtg  34920 tgtgtgtgtg tgtgtttgct tgggagggga gtcgggctgg agctggccag g ccgcagcct  34980 ggggaccttg tgattccagc agggatgtgg gccgagggtc ccgccttact c atttcgggt  35040 cttgctcctc tgtcctggct ctacagactc ttccagctgg agttggaggc t gacgcccta  35100 gtgaatttcc atcagtattc ttcccagctg ctacccttct atgagagctc c cctcaggtc  35160 ctgcacactg aggtcctgca gcacctgacc gacctcatcc gtaaccaccc c agctggtca  35220 gtggcccacc tggctgtgga gctagggatc cgcgagtgct ccatcacag c cgtatcatc  35280 aggtgagcaa gggaacaaga ccatttggac aacgtgtgtg tacctgcttg t gtgggcagt  35340 gggggccgca ggcctcggtt ccctccata gttgactta aaaaggagca g ggcctggca  35400 tggtcgctca ctaacgcagt cccagcactt tgggaggctg aggaggagg a tcacttgag  35460
```

```
actaggagtt caagaccagc ctggcaaaat agcaagacct tgtctctacg a aaaaattaa   35520
aaaattagca tgtgtctata ctcctagcta cttgggatgc tgaggcagga g gattgcttg   35580
agcccaggag ttagagttta cagtgagcta tgattgcacc actgcacttc a gcctgggtg   35640
acagaatgag accttgtctc taggaaaaaa aaaaaaaaaa aaaaaaaggt g ctgcgttgc   35700
taccagatta aaatgtaaga aggacaatgt aatgtttcca gagtccggag t gctcaccag   35760
gtgccaggtc tgtgggagct gatttctacc caccatgaaa ttgaattttc c caaccccca   35820
caagtatcg tcattttatt ttactttatt ttattttatt ttattttatt t tattttatt   35880
ttattttatg ttacgttatg ttattttatt ttgagacgga gtcttattct g tcacccagg   35940
ctggagtgca gtggcgcgat cttggctcac tgcaccctct gcctcctggg t tcaggtgat   36000
tctcctgcct cagcctccgg aatagctggg attacagtaa tgtgccatca t gcccgggta   36060
attttttttt tttttttttt tttttttgag acggagtctc gctctgtcgc c caggctgga   36120
gtgcagtggc gcgatctcgg ctcactgcaa gctccgcctc ccgggttcac g ccattctcc   36180
tgcctcagcc tcccgcgtag ctgggactac aggcgcccgc caccacgccc g gctaatttt   36240
tttgtgtttt ttagtagaga cggggtttca ccatgttggc caggttggtc t cgaactcct   36300
aacctcaggt gatctgccct ccttggcctc ccaaagtgcc gggattacag g cgtgagcca   36360
ccatgcccgg cccaggtatc atcattctag agagagctaa caggacttgt g caggtcact   36420
cagccagaga gggtgaaaga gggcttgga tccttggtgt ctgcccaggc t gctcttctg   36480
gaagctgaag gcctcctttt gtgaatccat tcagccagca gatggagcag c tgttgcccc   36540
tggtgagggc actgtcccca cccttgcaca gggcaccagt tggccatctt g tgcagaggt   36600
agccacacct cctctgagtc tctatcctag atagctcagt taagctccca g gcccagaac   36660
tcaaaacctc actgctggcc gggcgtggtg gctcacacct gtaatcccag c actttgtga   36720
ggccgaggcg ggtgtatcac ttgaggtcag gagtttgaga ccagcctggc c aacgtggtg   36780
aaaccccgtc tctactaaaa atacaaaaaa ttagcaaggc gtggtggcgc a cgcctgtaa   36840
tcccagctac tcgggaggct gaggcaggag aattgcttga cccagaggc g gaggttgca   36900
gtgagccgag attgtgtcac tgcattacag cctgggcaac aagagtgaaa c tccacctca   36960
aaaaacaaa acaaaacaaa acccctcact gcacttagt ttccaggcgt g cttttggac   37020
agcactgtct catctcacca tcactctgtc catttcctgg ggcaggcaca g cagcttgtg   37080
tcgataagga tattgacgcc cagaaaggtt aagtgaattg cctgaggcta g tgagatatc   37140
cgtgttctgt gacccttttcc tgtgccacca ccctgcccac ttcctgctgg t gtggccctg   37200
ggcccatct cttgtacgag tgagcaaact gaacagaaac ctgatacagg t cacatcaga   37260
tataattaca ttcaaatcag cccaactagc tgagtggcgg gaatgctctt g agctcaaat   37320
aaaccagaaa gtccgagttt ccgagtgcac ttccctgcat gtgcacttag g tccccctgc   37380
caccttgtac cacacctgct cacctctgct caccctggcc ctctcctgca g ctgtgccaa   37440
ttgcgcggag aacgaggagg gctgcacacc cctgcacctg gcctgccgca a gggtgatgg   37500
ggagatcctg gtggagctgg tgcagtactg ccacactcag atggatgtca c cgactacaa   37560
gggagagacc gtcttccatt atgctgtcca gggtgacaat tctcaggtgc t gcaggtgag   37620
caggggagg ggcagggtga ctggtactga tacctcccgg tgtccacggt t ccctttggg   37680
cccctaggct caggtgtcac tctcaggcct ctcactgtcc cccattggtc c ttgaggcct   37740
gagctccttc atggagggtg cagacccctc cctggctctt cctcccagc c cttttccag   37800
gagccacgtc ctcagtctct ttgcttgata aacctgggga cggcctccaa c ccagcaaaa   37860
```

-continued

```
taaaccccaa aaaaggccca gctccagtca gttagttcag ttccactttt c ctgagcaca   37920
aactgtgagc cagatgcctg cctggagggg ctcgtgggcc agcgggacct g ggcttaacc   37980
ttttgcaagc ttgtccaatc tgtggccctg caggctgcat gcagcccagg a cggctttga   38040
atgtggccca acacaaattc acaaacttttc ttaaaacatt atgagatcca t gcatggacc   38100
tttttttttag atcagctgtt gttagcgttc atgtattta tgtgtgaccc a agacaattc   38160
ttctgatgtg gcccagggag gccaaaatat tggacaaccc tattttacag g aattcaaac   38220
caagcaaacc aaactgtctc cagttcctgt aggcatttgt gccagaggcc c tcctgttaa   38280
cgttttgat tacctgggca aaagatgtga ttttttaatt gtgggcaagc a gatggggtg    38340
atactattaa atagctattt catatattag attgaacaga aaaggcagga t gttggatta  38400
tgttttattg tctagaatta gaaaattctt ctaaagatca tgttctctct g ccttggcat  38460
cagaatgcaa ctacgttata ccagaaaatg tggattcctt tttttttttt t ttttttttt  38520
tttttgagac agagtttccc tatgtctccc aggctagagt gcagtggtgc g atctcggct  38580
cactgcaacc tccacctcct gggttgaagt gatgctcgtg cctcagcttc c tgagtagct  38640
gggattacag gcatgtgcca ccatgcctgg gtagtttccg tattttagt a gggatgggg   38700
ttttgccatg ttgcccaggc tggtctccaa ctcctggcct taagtgatcc a cctgcctca  38760
gcctcccaaa atgccgggat tacaggtgtg agccactgtg cccggcccag a aaatgtgga  38820
ttcatatctt atgcttcttg ctctcaggga agggaattct ccacccactg t tgaactcca  38880
cttttccacga gaatcctctg cgcacccagc atggtgccgc gcagaccctg c ctccatgcg  38940
ggggtgtgca cacccgcttc tcgatagtca tgcacgactg cagctgtcct t tatccggtg  39000
ctgattggtg cctgaccttg aactgagtgt tgtatgtgtt ccagttaatt c ttagaatac  39060
actcatgggg tggaggtcat tattcccctt tcctctccga agaaactgag g ttcagtgtt  39120
gttaattaag aagcgtgccc agggagggcc acaaagctga gagagtgggg c ttgaccta   39180
cattggcctc gatgccagcc ctttgctctt cctgctgtgt ctctggcctg c cttcaggtc  39240
cagtgggact gctgtgaggt gaccctggtg tcacatggga cactgtggt t gtaatgaac   39300
ctcatgggga cagcactgag ccaaaagtga gacagtaaaa ccctcctagc a cttctttt   39360
ttttgagaca gcatctagct ctgtcgccca ggctggagtg cagtggtgtg a ttgtggctc  39420
actgcagcct caacctcctg gactcaggtg atcctcccac ctcagcctcc t gagcagctg  39480
ggactacagg ctcgtgccac cacatgggct aattttttt tttttttgaga c ggagtcttg   39540
ctctgtcgcc caggctggag tgcagtggcg cgatcttggc tcactgcaag c tctgcctcc  39600
cgggttcatg ccatcctcct gcctcagcct ccagagtagc tgggactaca g gcgcccgcc  39660
accacacccg gctaattttt tttgtatttt tagtagagac agggtttcac c gtgttcgcc  39720
aggatggtct tggtctcctg accttgtgat ccgcctgcct cggcctccca a agtgctggg  39780
attacaggcg tgagccacca cacccaggcc acgccagcta atttttaaaa t tttttggt   39840
aaagatgggg tctccctatg ttgccgaggc tggtatcaca ctcttggtct c aagtgatcc  39900
tctcacctcc cagtgtgttg gaattacaag catgagccac tgcgcctggc c cctggctct  39960
cttttaata ctgctgttct ttcattgaaa acatagtacc tgcatgtaga a aaaaatcag   40020
tcaggacaga atgaaaagca agaatcattc ccacctggac ccccagtgcc c atcctgaga  40080
tacagctacc ttttaagttc cttgactcag aaatgtttca tgtgagccac a gtcatgcca  40140
ggtcgacccc ttccctccca tccacactgg cacttggctt tcctggtgct t ctctttacg  40200
```

-continued

```
ttcttttttt ttagacagag tttttgctct attgcccagg ctagagtgca a tgatgcaat   40260
ctcagctcac tgcaacctct gcctcctggg ttcaagcgat tctctttcct c aggttcctg   40320
agtagctggg attacaggtg cctgccacca tgcccggcta attttttgtat c gttagaaga  40380
gacgacattt caccatgttg gccaggctgg tctcaaactc ttgacctcag g tgatccacc  40440
cacctttggcc tcccaaagtg ctaggattac aggcatgagc cactgcgccc g gcctcttta  40500
cgttcttatc agcatcctat ggagtcaaac ttcccttcct ctttcatcag c tccttggaa  40560
ggaacgcagt ggctggcctg aaccaggtga ataaccaagg gctgaccccg c tgcacctgg   40620
cctgccagct ggggaagcag gagatggtcc gcgtgctgct gctgtgcaat g ctcggtgca  40680
acatcatggg ccccaacggc tacccccatcc actcggccat gaagttctct c agaagggt   40740
aagacctcct cccctcccca tctgctggcc tgctgggctc cagctctcct g tcacctgtc  40800
ccgtgcctga ggcaagcagt atccaccata gatcttagca tctccagcct c agagcagag  40860
gccccgggtt cacaagcctc attaggcccc gcctggccca agaaggtgc t ccatcattg    40920
tatcatgggt aggaatctcg gttcacaagt tcagctgtgc aaggaggaga c tttaaaatt  40980
tttctggctg ggcgcggtgt ctcacgcctg taatcccaac actttgggag g ctgaggtgg  41040
gcagatcacc tgaggtcggg agttcgagac cagcctgacc aacatgaaga a accccatct  41100
ctactaaaaa atacaaaatt agctgggcgt ggtgacacat gcctgtaatc c cagctactt  41160
ggaaggctga ggcaggagaa tcggttgaac ccgggaggcg gaggttgcag t gagccgaga  41220
tcgcaccgtt gcactccagc ctgggcaata agagcgaaac tgtctcaaaa a ataaataaa  41280
taaataaata aataaataaa taaaaataaa tttatttaat gtaccttaat t cctaggagt  41340
gaatctccct ctataaaact ggagacaacc aatcttagcc ctctttgggg t ctcctctt   41400
ccagctcccc tccaggtggt gctccagttc tggagtctga tgcaaccca a ggcccacct   41460
ggcccctcct ctaacccagc ccagcctgat ctgaacagcc ccccgatggc t tcagtgctc  41520
cttggtttct tgtgtgccca gctcaaagcc tgggaaatgc ttggtaaggt g gccgagtgc  41580
ccgtccacct agatgcctct ttcctttctg gctggtggca cgttgggagg c aggtacagg  41640
ctcatgtttt gggagcctgg gaaccctggg tgtcaggaaa attgtcttca a aggggtagg  41700
ggatgagata aaaagataaa tgaatatctc aaatctcaaa atactatcta g gccaggcgc  41760
ggtggctcac acctgtaatc ccagcagttt gggaggccaa ggtgggtgga t cacctgaag  41820
tcaggagttc gagaccagcc tgaccaatat ggtgaaaccc tgtctctact a aaaatacaa  41880
aaattagcca ggtgtggtgg tgtgtgcctg tagtcccagc tactcaggag g ctgagacag  41940
gagaattgtt tgaaactggg aggcagaggt tgcagtgatt tgagattgtg c cacagcact  42000
ccagccaggg cgacagaaca agactccatc tcaagaaaaa aaatactatc t aacaggaac  42060
aacatctaga atgaatgaat gagccaatga gtccttcgat cctggcactg t gctaaagca  42120
ccagcctcac cgaaatgaat aagccactcc aggacaggag acacccccagc c acccagaat  42180
ctcatagcgc agtgccagac aagcagtgag aaggcatgga cgggcagcac t caggcaggg  42240
aggctggcac ttgtgcctgt cctcaggttg ttccttcctc tgggagctgc a tccaccttg  42300
ctagccccat ggggcattgc tagcccttct aagggctgga ccaagcctgg a caaaccctc  42360
cttttccttga atctcccaag cacagccaga atgagctaga gctttcagaa a tacttgacc  42420
aaacagagaa gataccaaca cccccagccc cgcagtcagg ttccccattt g caggttgtg  42480
acctgagtgg acaccaggtg atgctcttct ctacccagag ggctggcaca t ggccccact  42540
cttgcttgtc tccagccacc ctgagctgta ctgggcagga gctgtaattg a ccagttttc  42600
```

```
tctctcttca aacaacctca gccctcaccg gtccctctgt ccccacacag g ccatcctgg   42660 gtgggtccag cgtcccatca cataagagga tctttgcaca gaagacaaag g aagaggctc   42720 ctaccttgag tggagcaggg agatcccttg tcgacttggc agccagcaca g ccctactcc   42780 aagaatccca cggcctcagt gttactgaca agtggttccc tcacagctca g actaggagc   42840 tccctcgctg tttttctttt tcttttcttt tctttgtttt gtttttgaga c agagtttca   42900 ctctgtcacc caggctggag tgcaatggca tgatcttggc tcactgcaac c tctgcctcc   42960 caggttcaac tgattctcct gcctcagcct cccaaggagc tgggattaca g gtgtgcgcc   43020 actatgccca gctaattttt gtattttag tagagatggg gtttcatcat g ttgaccagg   43080 ctagtcttga actcctgacc tcaggtgatc tacttgcctc gccctcccaa c atgctggga   43140 ttacaggcgt gagccaccgc gcctggccac ctctgctgtt tttcaatgca g ctgaccttt   43200 cccacaaagc tcggtttgtg cctgcggttc tcagatggtt aagccctgc t gaggaaggg   43260 aaacagataa tcccagacag tgagatggag gctgagactg aggatgcctg g gggctgcac   43320 taggagctca gagacggcat caggcagctg gagttcaggg aaggtttggg g gcagcagag   43380 cccgagccaa gccatggaca ctagccggag ctggccactc gggtgaagac t tgggggct   43440 ccagagggcc cagggaaaga agctgggcct gactccatgt gcctagtgct g agcaccaag   43500 cgctggcata agggctgtag ggagctgggc agcataaatc ctgggcctgt g ctgggcacc   43560 cctaataata gagaacagca gctgaacact aacgctgtcc cagccaccgg c ttagccttc   43620 atgtgggcta tttcactata gcccagagag ctgatgtatt ttattccccc t ctaaagctg   43680 agggccaagt gtggtggctc atgcctctaa tcccagcact ttgggaggct g aggcaggag   43740 gatcgcttga gcctaggagt ttgaggctac agtgagctat gatcatgcca t tgccctcca   43800 gcctgggtga caaagggaaa tcctgtctca aacaaacaaa caaaaaacag a tgaggaaac   43860 cagggcttag agagattaag taatttgctc aaagtcaggc agtcagtaag t gccagacct   43920 gggaattaaa cccatgtggg ctgtcctagt aattgcacta aaaaaaaaaa a aaaaaaag   43980 ctttattgag atatagttcc tattccatac aatccaccta ttgaaagtat a caatgattc   44040 tgatatatta tgtttatttt ttccaactgt gatagattat atataacata a aatttgcca   44100 ttttaaccac ttttgttttt tgtttttgag acagagtttc gctctcgttg c tcaggctgg   44160 agtgcaatgg tgtgatctcg gcttaccgtt acctccacct cccgggttca a gtgattctc   44220 ctgcctcagc ctcccgagta gtagctggga ttacaggcat gcaccaccat g cccagttaa   44280 ttttgtattt tttagtagag acagggtttc tccatgttgg tcaggctggt c tcgaactcc   44340 cgacctcagg tgatccaccc accttggcct cccaaagtgc tgggattaca g gcgtgagcc   44400 accacacccg gcccatttta accacttta agtgtacaat tcggtggttt t aatcacatt   44460 tacaatgttg tccaaccatt accctttct aaaactttc ttatcacctc a aacagaaac   44520 tgtaaccatt aataactccc gattctcccc tccccacagc ccccgataag t cccatatcc   44580 tctctgtctc tcgaacttg cctgttctag aacctcgtat cagtgaaatc a tacagcgtt   44640 tgtccttttg tgcctggctt atttcactta gcatgatgtc ttcaaggctc a tccatgttg   44700 cagcacgtat cagaatttcc tttctttta aggcagaata ctattttgtt t atccattca   44760 gtccttcact gatagacgcc tgggttgttt ccaccttttg tctgttgtga a gaatgctgc   44820 tgtgtacatg ggtctgcaaa tgtccattca agtccctgca ttccgtcctt t gatacttcc   44880 gacctcaggt gatccgcctg cctcagcctc ccaaagtgtt gggattacag g cgtgagaca   44940
```

```
ccgcgcccag ccagaaaaat tttaaagtct tctccttgca cagctgaact t gtgaaccga   45000
gattcctacc catgatacaa tgatggagca ctttctttgg gccaggcggg g cctaatgag   45060
gcttgtgaac ccggggcctc tgctctgagg ctggagatgc taagatctct g gtggacact   45120
gcttgcctca ggcaccgagt agaaagcaat tgtgctcttt cccactctgt c atactgctt   45180
cctatagcat gcaggtcact gtgtgactca ctgacagtgt ggtaaggagg t ggagggtgg   45240
ctgtgtgcca ggcacagaac tgggctctga aatgcctggt cttccttaca c cccagccac   45300
tcctctcagc actctctcca tgttgctcag cttctggagg ccaccagtga g gaagctggg   45360
gcttgacttc aagcccatct gactctaaag ccagtaccag ggaggtgat c attgctggt    45420
ggcagcatca ggaaggcttc ctggaggagg gggttagttg tgccttgagg g gctcagtac   45480
agccttaacc atggtgagtg tgctggttgg gtttgctgaa ctttgtttgc a gtgatgctc   45540
tctgtaagca gtagatgaag ctccaagtcc tggcttcatc ccacgccacg c agaccctag   45600
cttctgctca ccaaccgggg cccctctctc accaggtgtg cggagatgat c atcagcatg   45660
gacagcagcc agatccacag caaagacccc cgttacggag ccagccccct c cactgggcc   45720
aagaacgcag aggtgagtgg atcctgaggt gggtgggtgg ggcaggggc c gggccccgc    45780
aggtcctcag ggccctcagg aagcaggttc ccgagaggac cctgaggcta g cacttgggg   45840
gctgaccttg cagtgggtgt gcaggcagag aagtccatga agagctggga t cctggcagg   45900
gctctgctgc tctctggctg ggcgggggga tccgccctgt gcctcagttt c ctcatccat   45960
gaattctgct ttggcgatgt gatgaagtca gcaaggcagt gtgtgacaaa a ctcggcaca   46020
aattgtaaag tgcttcccaa atagaaggtg gcgtgatgat gattgtatta t tagtcagga   46080
ttctctagag ggccagaact aacaggagat atatatatag agagagagg g ggtttatttt    46140
ttttattta tttttttttga gacggagtct cgctctgtcg cccaggctgg a gtgcagtgg   46200
cacaatcttg gctcactgca agctctgcct cccaggttca tgccattctc c tgcctcagc   46260
ctcctgagta gctgggacta caggcgcccg ccaccacacc cggctaattt t tttgtattt   46320
ttagtagaga cgaggtttca ccgtgttagc caggatggtc tcgatctcct g acctcgtga   46380
tctgcctgcc ttggcctccc aaagtgctgg gattataggc gtgagccacc g tgcctggcc   46440
taaaggggga tttattaagg agcattaact cacacgatca caaggtccca c aataggcca   46500
tcgcaagctg aggagcaagg aagccagtcc aagtcccaga gctgaaggac t tggagtctg   46560
atgtttgagg gcaggaagca tccagcacgg gagaaagatg taggctggga g gctaagcca   46620
gtctagcctt ttcacatttt tttctgcctg ctttatattc tggccgtgct g gcagctgat   46680
tagatggtgc ccacccagat taagggtagg tctgccttcc cctactgact c aaatgttaa   46740
tctccgttag cagcaccctc tcagacacac ccagggtcaa tactttacat c cttcaatcc   46800
aatcaagttg acactcatta ttaaccatca agatgatgat gatgatgatg g atgatgatg   46860
gtggtggtgg tggtgctggg cctagctgca cacacaggga gcctggctgg g catctcctc   46920
tgagttcttc ccctaagcta agctctgtcc tcctgggagg atggaggcct c tggtctcat   46980
caccaggaag cacagcttga cagagaatgg gatgcccag agttcatggc c tacttctca    47040
atgtgatggg ccaggaggga gggcactgcc agcctcaggg tacctctgca t tccaggagc   47100
cggacaccga gtcaggccct tccgtgtagg tttggtcact cattgtcatc a catgctgtg   47160
aggtggggac ttgcattccc atcttccacag aagccctgaa gtgcacatgg c tacagtgac    47220
ccatccaagc gcaggcagct gggatgagtg aagctgggct ttgggctcag g tctgtgact   47280
ccaaagccag gctcccctcc ctgttcccaa ggctctgcca gggatgtgca t tgccaaggc   47340
```

-continued

```
ccagtgagag gtgataccct tgcagggttc cagggaggga tgcagggagc g gggtgcttc    47400 aggacaggcc ccagaggagc ctttgcaagg agagtgggtt ctgttggcac t aggaaagga    47460 ccagaagcct cttaaaacag tcagcacatc tttggctttt tgtccctagt c ttgggatgc    47520 tgatgggatg ggaggcagtc taggccccc tagaactggg gcctgccct g gaatcctct     47580 tgctagcgct ttccaacatc ccagtacctg taggcctctc agagcagaag t ggcagtgcc    47640 cacgtgtccc ggggtgcggc agctccccga gtgcctgtgc taactcagcc t gaccgtctc    47700 ccgcagatgg cccgcatgct gctgaaacgg ggctgcaacg tgaacagcac c agctccgcg    47760 gggaacacgg ccctgcacgt ggcggtgatg cgcaaccgct tcgactgtgc c atagtgctg    47820 ctgacccacg gggccaacgc ggatgcccgc ggagagcacg caacacccc g ctgcacctg    47880 gccatgtcgg tgagcccagg accgcgtgtc ctgccctgtg ggccccggt g ggaatgcag    47940 gagggctgtc cggactggag ccctcctccc cactgtctcc ctcctatcgt c agctgctcc    48000 aaatcatctt cccacccaaa gctcagttca gaccctgact cctccctcag g aagccttcc    48060 aagtcccct ctcagcccaa ataacacca ctcctgtgt gctgtggtac c ttttccacc       48120 tgtgccccca tttggcactt gcatggcacg agagggaaaa atgacagctc t ggccataga    48180 ctggccctga gcaagccatg tcacctgtca gcctcgattt cctcatctgg a aaatggtgg    48240 tgtcaatact tatctggaag agttgtggaa aagttatggt ggacacttgg t caccctcta    48300 cagaatgtct aagtgacaca cgcagtacct ggcccgagtg agcatcctgc t tcccttcac    48360 tggtccgcgt gttgctctca tcttccctgg gaggctgtaa gatcctggca g gcaaagcct    48420 gagtgtgcag cccagcagcc tgtggcaggt gccaggcata ttcgttggtt t attatagaa    48480 cacagttcct gccctcaaag cccttactgt ctggttacac atctagagta t gaacatatt    48540 aaacctagca gaggaggacg ttactgtgtt acagacatat gtgtgtgcat g tattctttt    48600 ttttcgagat ggagtctcgc actgtcgccc aggctggagt gcagtggcgc g atctcggct    48660 caccacaacc tccgcctccc aggttcaagc gattctcctg cctcagcctc c caagtagct    48720 gggactgcag gcacgtgcca ccatgcccag ctaattttg tattttagt a gagacgggg    48780 tttcaccacg ttggccaggc tggtctcgaa ctcctgtgtt ggccaggctg g tctcaaact    48840 cctgacctca tgatccaccc gccttggcac cccaaagtgc tgggattaca g gcgtgagcc    48900 accgcgcccc accgtgtgca cgttttctat agcaataccg tatgtacaga a gtctgttta    48960 ctgagtctca gtgacagaac atgagagacc cccgggactc taaaagctga t tcaggacac    49020 attcagagac atcctgtttt ataccaaagg tcaaaacttg gaagagatgt t gttgcccaa    49080 aaggctgaaa ctataaatag tttcatttt gaaactgtgg acattttag c actgggtgg    49140 gcccttggaa tgatctaact cagcagttct caagtttttt ggcctatttg a tccctttat    49200 actctgaaaa attattgagg atcacaaaga ttttttaatc atctggattt t ctttatcta    49260 tatttaccat tttagaaatt taagtgtga aatttcaaa atattaattc a tttaaaaat    49320 aacaataata aatatatatg cctactatgt acccacaaaa attaaaatta a aattttttt  49380 aaaaactta aaaataact ggccagctgc agtggctcgt gtacaccagc a ctttgggag     49440 gccaagatgg tcagatcacc tgaggccagg agttcgagac cagcctggcc a acatggcga    49500 aagcccatct ctactaaaaa tgcaaaatta gctgggtgtg agacctctga a agggtatca    49560 cgtgttcaca ggggtcccca ggtcttactt taagaactgc tgatagactt t ggtcatctt    49620 catcccatct tcacagtttt tggcatattc atcaaccacc tttacaatta t gtacttaat    49680
```

-continued

```
cacctcttca aattggctta cttttatttta tttattttga dacagagttt c gcttttgtt    49740 gcccaggctg gagtgcaatg gcacgatctt ggctcaccgc aacctctgcc t cctgggttc    49800 aagcgattct cctgcctcag cttcccgagt agctgggatt acgttcatgc g ccaccacac    49860 ctggctaatt ttgtattttt agtagagacg gggtttctcc atgttggtca g gctggtctt    49920 gaactcctga cctcaggtgt tccacctgcc tcagcctccc aaactgctgg g attacaagc    49980 gtgagccacc gtgcccggcc tggcttactt ttaaactgac ttaaatttat t ttgagagaa    50040 atgttgcatc actaccataa atggccatcc atccatccag tgccaaccat a aaaggtaac    50100 caatgcaggg cgcggtggct cacgcctgta atcccagcat tttgggaggc c gaggtgggc    50160 gaatcacgag gtcaggagtt caagaccagc ctggccaaca tggtgaaacc c tgtctctac    50220 taaaaataca aaaaattagc tgggcgtagt ggtgggcacc tgtaatacca g ctactctgg    50280 aggctgaggc aggagaattg cttgaactcg gtaggtagag gttgcagtga g ctgagatca    50340 cgccactgca ctccagcctg ggtgacagag tgagactccg tctcaaaaaa a acaaaacaa    50400 aacagtaaca acaacaaaaa atcacagtta atgctgaaaa cacacacata t ctgtagcca    50460 tagaagtcct aatagaatgt gaagaactgt ttggaaaacc ccattctaga c ccacagctt    50520 cattctctag gcagggaaat cgggtcccaa gaagaggaag gtgacaaggc c agagcccac    50580 agttccaggt ggccagtgtg tcctctgaaa ccatgccatg ctctgcgccc c tgcccggcc    50640 tccaggtgtg gaaatgtgtg acgttcttcg tggggacact cccccgaagg c tgccattag    50700 gggcacgtgt gttcggttac ccctcaggga tgacaccctg gactgggtgg g caagatggc    50760 cttccctgcc ctcacccacc ctctccttgc tactcctgaa agccatcagc a gctgaccta    50820 ctgtgtcccc atggctcctg ggtcggggtc acagatgcac tgcatctttg g aggcggagc    50880 tggcagagca ggggcgagtc acttctagtt tctgcctggg ttcttacacc c tcccctgtg    50940 ggtgctttta agcctgtttg tcaggtcccc agccatcaaa tggcagactt t ggactacca    51000 gattgacttg ggtgggggtg aggagggttc cagtgtctcc ccgtgctgag g agaggcccg    51060 ctgggtgagt tgacaggttg gggctggcag ccaggggccc ctttgttctt c acttcccg     51120 gcagttgcac gtcttatcct ctctccatct ccaacagaaa gacaacgtgg a gatgatcaa    51180 ggccctcatc gtgttcggag cagaagtgga caccccgaat gactttgggg a gactcctac    51240 attcctagcc tccaaaatcg gcagacgtat gtgctctgca ctctggggct g gagtggggt    51300 gagggttggg tggatacagg gaccgaggag gagggaagtc ccaggcatca g gtgccagca    51360 tcctgtgctg acccgcccctg ctcagagctg ccaggagcac ctcgtactca g agagggggc    51420 ttccttaccc aagcacaagg gccctgagca gtagatgcag gcccaccacg g gcttgcta     51480 taccagcatc ctctcccgtg cagcgccccc cacctcaggg agctaagatt c ccagcaggg    51540 gtggggacag gagagccagc agcagccttc tttccccacc gttggggaat t cactgatgg    51600 aaccactggc tagaatgacc aagggtgcat gcactacact gcacgagctc t gggcatgcc    51660 tgtgtgggca gagtgcatgg ccatgtgctg cacgctcgca cagtgagcct t agcttcaga    51720 gctggacaga gcagatcctc ctcaccagag gcctggagcc cgctctggag g gtttcagca    51780 gctgtggggg tcactgtggg caggtacctg atggcagcag tgtgtgtgtg c cagtgcaca    51840 cgtgtgtgtc tgcatgcacc gcatctatga cctccttttc agcaatccca t ccatcaaat    51900 ggagtaggtg cccctggct ggctcattag tcccttgga accctgaact a tcacttagc     51960 attttttgaga atcactgaat gtggccatgg gattcctgct ttcttggctg g agtagaagg    52020 aaagaagggg ttcccacagg catcgggcag ggtgacactg acctcctcct c ccatatcct    52080
```

-continued

```
ccttccctgg ccttaggaag ctgcttggga tgtaccagcc tgggggcagc a ctccctgtc    52140 agggtgggct gaggcctctg gagcagccca cgtgcccagg gcctgggagc t gggacaggg    52200 gacggagtgt ggaaaggagg ggcctctcct ttgcatgttg acatcatttc t gatcctgtg    52260 ccatctcccc ttccccaaac catgacaagt tgtcaccagg aaggcgatct t gactctgct    52320 gagaaccgtg ggggccgaat actgcttccc acccatccac ggggtcccg c ggagcaggg     52380 ctctgcagcg ccacatcatc ccttctccct ggaaagagct cagcccccac c gatcagcct    52440 aaacaaccta ggtaggcctc gcctcccgac tccctcttct ccagctggtt c ccaggcccc    52500 tggatcacag caggccccac caaagcaaca ggatccctag gacggaagtc a ctaaaggaa    52560 gccgggggag atggggccgg agttgtcagc ctctaggcag ccagcaaccc a cagatccca   52620 gaggcctagg gtgtccctgg ctgatgtccc atgctccgtt gcccctgaga g gatgtgtcc    52680 tgcacacagt ctcaggcctg gcatttcca gtggcaccca tgaggtggct g ctgttactg    52740 ccctcctgtc cccagggcgt tcagggtggg cagtgaggag tgctgtcggg g gactggggg   52800 cccgggcccct ctggcttcac ctgtccctct ggcttcacct ctatcacact g tttgaatct   52860 cggttgggcc tgagacctgt gtgccccctt cctggccccg tggtgacttt c agacgttga   52920 atgtggccag gcagccagca tctgcccggg tgcattcctt ggtgcccagg g agacatccc   52980 cagactagac aggacccttc tctggacttt ctgtgggctg gcccactcag g gacctccat    53040 tgtttgggag cggggtcccc tgaacagagg gcagccagga gccagtcctt g gtgagccag    53100 acttcactgt ggaggcggca gcaccttcag ccagggtagc ccgaccaagc c tggaactct    53160 ggagaggcac cgtgactgtg gcttctagtc ctggctccac ctctctctcc c ctcccagga   53220 actccccctc cacctcccat ctttatctct caatttttgca ggcagtcacc c aagccaggc    53280 cggatggtgg gcctggggtg cggcgtcaga tgggtaacgc cctgggcctg g agaggccac    53340 cgagcctagc catgcggcat tagctctagc tctcactccc taatccgtcc t tcttagctg    53400 cgcacacacc acacgccccc tcccctgcac cctgtccccg gcctctctca g ccactcttc    53460 tgcttccctt gttcactgtg gagccgtgtg ccctggggag ggggagacac c gcttcgcag   53520 ccctcggttc tgctttgctg cttctagact ctgcacagtg gtgggggggct g tcagagttg   53580 gggtcacgcg ggctgctgca ccaggcacct ggggactggg ctgcttgtca g gaggggcag    53640 ctagtcagtt gggtggacgt caggcaggcc ttggacacaa aggaagacat g gacagagtg    53700 gatggtgggc ctgatcccgg aggccactgg gatttccaga cctgggatca g gacgaggga   53760 tgtctccttt catccatgga cttaaacccc gaggaacgtc ctgactcagc c ttttgacta    53820 aatgaccttg ggtgaattat ggaccctctt agagcctcac ctgtcaatag g gaataagaa   53880 ttcttaggcc ccaggtggtt attgcagcat cggctccgat gcaagaagaa g cactttgtc    53940 tgaagaggac acgcaagggt attcatgcct tggggtttca agaggaagag a ttgagggga   54000 acctgggagc tggctgggca gggtggggag cccttcccag agcagtgggc c cccctttcc    54060 actccagccc atttctctcc tgtggcctgt ggctcagctt tctcctggga c agagtcctt    54120 cctgtgggga aggacagat gacaggggga gtgggggggat gagggcgtgg c cgtgggcga    54180 ggcacagccc aggtttgatc tagggacctc tgggtagca gggcttgggg a cccacctga    54240 ccacagcatg ccctgctctg tgcctcacag aactacagga tctcatgcac a tctcacggg    54300 cccggaagcc agcgttcatc ctgggctcca tgagggacga gaagcggacg t aagtggatc    54360 gagatcgggg gcagagcggg gaacgtgtgc gctttcctgc ccctcaccca c cccctgttg    54420
```

```
tgggctcagg gctttactct ctgcaccctc acagccggcg aagtggctct g ctcctagtc    54480 ttatagttct cagcagagac agaacatgga gagcctgtgt cgctcgttca t taatgctgg    54540 gcggtgcagg ctctggagac cagcccaggg tgccaggctt cttggacttg g tggggctgg    54600 cgcagtgttc tggcctccct ccctgatctc cttatggcta aagaggggg a gatgcctgg     54660 gtcccccctg ggagatctc agcagctgct tcccactgct cctactggct t ccttaacca    54720 cctcccactg cagaatagtg gcgtgggctg ccttccccag cacctgctgt a tacctagtc    54780 ccattgtaag aggcgggcct gggtgacagg atgcaaagag aagacgccca g gccttgccc    54840 ttcaggcata atcccgggtg cttgaactca gtgccagctg gcacggcaag g taccaggac    54900 aaatgcgttt ccagccactg tgctgtcgcc acctcccttg attgctgcag t tgattcatt    54960 tattctttat tagtctctca tgttcctaat agccttccca gggaggaatt t gtaaccttg    55020 ttttacagat gcagaacctg agcccctgag aggtgaagtg acttgctcaa g gtcacacgg    55080 agtgagtgtc agggtggcaa ctcacagccg ggtcttccga acccacgtcc t ttgtgctac    55140 cgcaggctct ctctgggttc tctgtggact ctatacctag tgccagccct c tgcagggaa    55200 agctctcttc tcagaatcag aggcagctcc actcccaggg ccaggcagtg a tcgtgcagc    55260 tctgtgggtc ctctcacttc gcactcactt ccatgctacc ctgttgtgtg c cctggaggt    55320 tccctgccc catcagcatt ccctcccctg tgccccctgc atgctcttgc a cgcgggcac    55380 acgcacacac acacgcacac atgcacgcac acacccac atgcacatgc c tgcgggttg     55440 cccacatgca tgtgttgccc acatgcaaac acatggacag gcacacacat g cacacatgc    55500 aaacacacgt gcatgcacac acatacacat gcgcacacat acacatgcat g catgcacat    55560 ggacacccac acacatgcac acacatgtac acacatgcat gtacatacac a cacctgtgc    55620 aggggctgag gtgaggcagc tgcacctgaa gggggaccc acatttccca a gggaggaaa     55680 agcagattcc ccagattctg gagcctcaga accctgcctg gagcgggct g aggcaagag     55740 tcaggagacc cctcggtagc tccccacttg ggccttccaa gctacagagc c ctgcgccct    55800 ctgggttgat ctctgtcgcc agccccgcat cttcgggagt ttgctttggc c tccagcaac    55860 agtgtagtct ctcccctgcc acctctaggc ttgctgtggg gctgggtacc t ggtccagga    55920 aaagacccct agaggtggga cccgggcctc ctccatttat cagccctctt g gcacctcc    55980 tgcatcccct tgacacacag cgctgcccag agcagaggcg gcttctgccc t ggtggagct    56040 tccaggtcag cgcaggagag agtaaaagaa agattgcgaa tggaatggaa g cagcctcca    56100 ccaggaagca ggtggagcag caggcgggct gtgagggagg gtctcgatgg c atcagggca    56160 ggcttctctc agcttcatca agctgagatg ggaagatgag aagatcagag g aaggttcca    56220 gactgaacca accacaaagg cattccccca gggcatggcc aatgaggaca g gcaggatgt    56280 ggggagacgt gtcagggcgc gctggagagc atgtgactca ggaggcggca g acctgggtc    56340 caggtccagt ccgcatccat atgacttggt tcccgtcacc taacctctga g ctacactcc    56400 ctccgtcact caaaaatatg cacagagagt aggcgcagtg gctcctgcct g tagtcccag    56460 ctactcggga ggatcacttg agctcagaag gttgaggctg ccgtgaactg t gattgcacc    56520 accacacacc agcctgggtg acagagtgag acctgtctc tataaataaa t aaataaata     56580 aataaggctg ggcacggtgg ctcgtgcctg taatcccagc actttgggag g ccgagacag    56640 gcggatcaca tgaggtcggg agttcaagac cagcctggcc aacatggaga a accccgtct    56700 ctattaaaaa tacaaaatta gctgggtgtg gtggcgggca cctgtgatcc c agctactcg    56760 ggaggttgag gcaggagaat cgtttgaacc cgggaggcag aggttgcggt g agccgagat    56820
```

-continued

```
cgcgttattg cactccagcc tgggcaacaa gagtgaaact ccgtctctaa a taaataagc    56880
acagggatgt cagggagggt ctgcctcaga ggcgtttggg acaatgacat g agctaatgc    56940
tggtagcacc cctcccatag cccctggcat gaacctctcc cttcctccct g cccctcct     57000
cccctgcttc ttccaccttg tgtggaggcc ctgatactct gtcactgccc a ttcctggcc    57060
tggctgtagg gtccccgccc ctccttcccc agccttattt aattccaaca g actttatca    57120
ggcacctgct ttggatcagg cctgatactg accaaaatca ggtgtcccaa g ttggggaga    57180
ctggccgaga tcctgctggg atggcgcctg gtcagtgatg ctatccccg a ccttcctt     57240
cccttctct gttgcactct ccagcccctg aaatactaga catttgttcc t ttactgccc    57300
tcaccccac cctcgctgtc ctgcatagga cagaagttcc tcgggtccgt c tgggtctgt    57360
ctgccaggac acagctgcag gggacaaggg ctatgagggt ggatgtaaag t actgggctg    57420
tggcaggacc ctcctctctc ccactgctgt tcccactgca gccacgacca c ctgctgtgc    57480
ctggatggag gaggagtgaa aggcctcatc atcatccagc tcctcatcgc c atcgagaag    57540
gcctcgggtg tggccaccaa ggacctgttt gactgggtgg cggcaccag c actggaggc    57600
atcctggccc tggccattct gcacagtgag ggcggcccct ggggatgggg c caggcgggg    57660
ctgagacctg tgtcctcaag gggccgagtt tgtcttcagg gctttgcaaa a agagagtgg    57720
aggagtagag gagggctata agcactttga ggaggcaggg gcggggctgc a ggtgctgag    57780
gtcccaggct ggaaggagaa gggctgggcc catgggcttg ggtttgggga t cccccgccc    57840
tctggccaca gagggtagag ctggctgtgt gaaattttgg cataggaagc g tttcctatc    57900
gactgcctta acccctcctc ccctcacccc tgcaaagcag gcaccagggg c cacacagcc    57960
tgctgcacat aaggaatccc attcccaggg tgcacgcagc aggcagtctc a ggaatgagg    58020
agccactgag cctcaggatg ccagagccct cgcctgcaca cttcatttta c tgggaaatt    58080
ttactgggaa attaagttcc caggtgggga gggatgacgt gaagtcacat a gctcatcca    58140
tggggtcgct gggctggagc acagtcccct agactcccag cctggcacct c ctaggccac    58200
agggcactgt gtagtctcct ttcactgccg cttttgcgaag gcgcctggct t gctggacag    58260
atagccgggt ggtcagtgtt gtgacggctc ctctgtggag ctgtctgagc t tctaggtgc    58320
tgacaggtgg ggaggggcac tgccagatca gggtcctcag ctcccccaa c ccctggac     58380
attgtcctgg gactcaacat gtctgactgg tgccctgcc cctgtgctgg t cagattcca    58440
ttttctccag agcgccccca catctggatc ctggtcatgc aaagtcttgg a ggtgcccgg    58500
ggaggactcc ccaccctagg gtgggtatca gggcctgtgg gccaggcctg t gttggatgc    58560
tggggatgca gagctgagcc aggcataccc cagcctcagg agcaggggc t cagccagtc     58620
caggaggtgc tggggacaga gtcccatggg cggaggagga gagtcatctg t caagttgcc    58680
gggacgttag tgtccacggc ggtttattga ctggtatttc atttccttt g atgattctc    58740
accatagccc tgcggggtga gcagatgggg aaactgagaa ccagagagga t cagccagtg    58800
aattgggcag tcaggactgg gtctccagca gtgtgcccag ctctctaccc c agcctcagg    58860
gtcccagcat cccctctctg gtcttccaca gggtccaagg gcgggcacga g gtctgagca    58920
ggcagactgg gcagagtcct agcttcttct ccaaaagggc cacgtccttc t tcagggacc    58980
atttcttccc catccggggt cttgagactc cagggggcca tggaggggat t tgagaggtc    59040
tcctggctga tcctccggtg tggcagatg gcctcctttc agctaccctc t gcttgtaca    59100
tccctggccc tggggaactc actgcctcac gggggaagtg gggcagcttc t ccttcctgg    59160
```

```
aggtgcagcc ggccccttgg ccctgtctgt tctgaaggct caaaggacag g gctattcct   59220 tgttttctgt gacaaacaac gtgggtctag cttttataag cttttactct t gaggggctc   59280 ttctttaagg aaaataatac aaaatcatga atacaagatg aagtgcagag c cgtggggct   59340 tcagtggttt ttgagtctct ccgttgccca ggctggagtg cagtggtgca t cttggctca   59400 ctgcaacctc cgctcccggg ttcaagcgat tctcctgcct ctcagcctcc c gagtagctg   59460 ggactacagg cgcccgccac cacacctggc gaattttttgt attttttaata g acgggtttt  59520 caccatgttg ggcaggctgg tctcaaactc ctgacctcaa gtgatccacc t gcctcagcc   59580 tcccaaagtg ctgggattac aggcgcgagc caccatgtcc agccggaagg a ggtttctct   59640 ctgtctgtct gggaggttgc aaaggaaggg cccagaattt gggtttgctt a ggcctcggt   59700 aaacccgctt cctcctgcca cctcctgcgt tcaggcgctc tgcaggctgt t ctacgggag   59760 ccctgcgtgt ggccgctgca tctccccgcc tctgacccct tgttcctag g taagtccat   59820 ggcctacatg cgcggcatgt actttcgcat gaaggatgag gtgttccggg g ctccaggcc   59880 ctacgagtcg gggcccctgg aggagttcct gaagcgggag tttggggagc a caccaagat   59940 gacggacgtc aggaaaccca gtaagccct ggcgcactgg ggccgtggcc g cagctgtgc    60000 ccactgtggc tgttccctgg ggacagaggg ctccctgtcc tgctgaggga g ggggaagag    60060 cgccccacgc ttgaggggag cagagggaac ccccttccca gggaggcaga g ggctggggt    60120 gtggctctca cttgggcatg cagacacctg ctgagcgcag gaggggcgtg g cctggtggg    60180 cctggctctg ccctgcctgg ctctgccctg cccggctctg ccctgccggc t ctgccctgc    60240 ctggctctgc cctgcccggc caggggtctg gggcttgcct ggagagagcc t gggccaccc    60300 ttctctgaga ccacctgggc agaggctggg ttttttgctgc ccaggcaaaa g gaacccact   60360 ggcctttcaa atgacacggc taaacatttt ctcacatttc agacagcact c gctcccagg    60420 atcggactac taggttataa tcagagggct tcagtcttac ctttaattta a ggcctacaa    60480 gacttgaact aatttaagtc agactgaagg agaaagtcac atttccagga a acatttgtt   60540 tgggaagccc aaatcctagg actaagcaat gcatcccgtt cggggctgga t gaatggtgt    60600 gttccaagag gagtgttttg agcatttctg agtgattttt tcatattttg a aagtgagtg    60660 tcccccagtt tagggggccc ggcatcccct ctgcggtctt ccctagggtc c aaggccagg    60720 gaccttcaat ctttttttcc actctgtggc ttgtctttct gctctgtggt g tttctaggt    60780 ttttgttttt tgtttttttgt tttggttttg gttttggtgg cccatgttct t aatgaggta   60840 gataatattt ataaatattt ttcttcttgt agtttgtgat ttttttccttt c tttctttct   60900 ttttttttgaa acagggtctt gctgtgggc ccatgctgga gtatattgct g tgaacacgg    60960 cttactgcag cctcgacctc ctgggttcaa gcagtcctcc catctcagcc g cctgagtgc    61020 ctgggactac tagcatgtgc caacacatgt attttttgta gagatggggt t tcaccatgt    61080 tgtccaggct agtcttgaac tcctgagctg aggcgatcct cccgccttgg t ttcccatta    61140 caggcatcag ccaccatgcc cagcctagtt tgtgcttttt atttctcgtt c ataaacccc    61200 tttgctgccc ccaagcagca cacgattctc ctgtgtcgag ctggaaagct t ctagatct    61260 gccttttaca ttgaggtctt ttatcaacct ggaattgatt tttgtatgag g gtgaaatcc    61320 aagatccaat ttaatgtttt ccacgtgatt ggccaatttt tcccagcccc a tctgtgaag    61380 tctgtccttc cctccgcttc ctcagcagtg ggtcaagcat ccctctgctc t tggatctgc    61440 tccaggctgt gttttgttcc actggttgga aagctgtctc tgtgcccgga c cacagagca    61500 taaaaaacta ccgctgtgtg gtgagtcctg gtgtctgggt ggcagatcct c caccttggc    61560
```

```
cttcttcaaa aacatcatgg ctattcttgg gggcagtaga gagaagtgga t acaagcata    61620 gaccctgaag tttctacctc ttctcaaaaa taggaatatg ccaggcatgg t ggctcaagc    61680 ctgtaatccc agctctttgg gaggctgagg caggaggatc acttgaggcc a ggaggtcga    61740 gaccagcctg gcaacatag tgagaccctc atctctacaa aaatttaaa a ctaacaatt     61800 agctgggcat ggtggcacta tggctgtagt cccagctaat tgagaggctg a ggtgggagg    61860 atcacttgag ccccggaggc tgaggctaca gtgggctgtg atcccatcac t gcactccag    61920 cctgggcaat agagtgagac cctgtcttaa gacaaaaaaa aaaaaacaaa a acaaacaaa    61980 ctcacaaact ataaaagaa aaatatttta taaattctac tccattaaga a catgggtcc    62040 atccaaataa ataaataaaa caaaacacc ataaagggga taaaaagaca a gccacagag    62100 tgggagaaaa gatttcgaat ccatacatcc atcaaggac tcattttcaa a atatgaaaa    62160 gatcattcag aaatgctcaa aatagtaacc accattttac tttctcttcc t atgagttta    62220 actgctccag gtactgttaa gtaaaatttt tagggataa ttgatttgga c caggattct    62280 gtaccaggcc caacagaaga aacgaatatg gagtcattca tgccaagtga a cctagttag    62340 cttaggcgta tacccatgta acaaatagct gagttctggt tagctacaac a gctaagctt    62400 taatcaatca tagatggcca cctgattcaa acaaggcaaa ccaattaagc t ccacacctc    62460 actttggttt tcagcccatc aacactgcct gaccacgttg caggccagag t tctttgaac    62520 ctattctggt tttgtggcct gcctgactct cagttcatca ataaaagcca a ttaacatct    62580 ttaaatttgt tgcaatttta tctttgaccg taccttatgt aagtggaatc a tacagtatt    62640 tgtctttttg tgactggctt atttctttct ttttttttt ttttgagatg g agtcttgct    62700 ctatcaccca ggctggagtg cagtggcgcg atctcggctc actgcaattt c tgcttccca    62760 ggttcaagtg attctcctgc ctcagcctcc ggagtagctg ggattatagg c gtgcaccac    62820 catgcccggc taatttttg tatttagta gagacagggt ttcaccatgt t ggccaggcc    62880 agtctcaaac tcctaacctc gtgatccacc cacctcggcc tcccaaagtg c tgggattac    62940 aggggtgagc caccgtgccc ggccatgact ggcttatttc acttggcatc c atgttgtag    63000 cgtgtgtcag aatttccttc ctttttaagg ctgaaaaact ccattgtctg t tggatacac    63060 gttttgcttc tccattcatc cattgatgga tattttagtt gtaaattgac t gctgtcaat    63120 gtcggatgtg caaatacctg tttgaggcct actctctctt actggtgcct t ctctagaga    63180 gaattctgat gggttcagtt tgatcatatt ttgtttaaga ttttttggcca g gcgcagtgg    63240 ctcacgcttg taatcccagc actttgggag gccgaggtgg gcggatcatg a ggtcaggag    63300 atcaagacca cagtgaaacc ccatctctac taaaaataca aaaattagc c gggcgtggt    63360 ggcgggcgcc tgtagtccca gctactcaga gaggctgagg caggagaatg g cgtgaaccc    63420 gggaggcaga tcttgcagtg agccgagatt gcgccactgt actacagcct g gcaacaga    63480 gtgagactcc gtctcaaaaa aagatttt gtgtccacgc tcgtgggcga a cttgacccg    63540 tttttttccta ttttgggttt tgaggaaata tttcctcttt ttattttct t ggaagagtt    63600 agtataatag tttatttga atttatggta gaacttgata gtaaattctt c taggcctgg    63660 agtttgcttg gtgggaggat ttttgatgat ggaattaatt tctatagtgg t tgtgagact    63720 gaccactcgg ggtttctaaa tacctttttg agttagtttt ggttaagtga g gttttctta    63780 ggaatgtgtc catttcatct aaatcttaa gcttattggc ttagagttgt t caaaatatt    63840 ctgtttttt ttttttttt tttttttgat gacggagttt cactcttatc g cccaggctg    63900
```

-continued

```
gagtgcaatg acgtgatctc ggctcactgc aacctctgcc tcctgggttc a agcaattct   63960
cttgcttcag cctcccaagt agctgggatt acaggcatgc gcaaccacac c taatttttg   64020
tattattagt agagacgggg tttccccatg ttggccaggc tggtctcgaa c tcctgacct   64080
caggtgatcc acctgcctcg gcctcccaaa gtgctgggat tacagacatg a gccaccatg   64140
cccagccgat tctccttttt ctaacgtctg cagtgtgtgt tggtgcggcc c ccttttctt   64200
tcctgatttt gataacagat aacagccatg ttttatcagt cttgcaacag g ttttttccat  64260
tggattagcc tttcaaaaaa accaacttt gctgaattgt gccccaagg t tggaccaat   64320
ctgacactcc tccagcactg ccggagagag cctgttttgc ggggatggtg c ggggagaag   64380
cccacctatc ccgaacagag gttggagtgg gcactctgct acccaaggcc c tggggtgtg   64440
aattgtgggg aaagggaaag gtggatgggc gggtggctca gccgtcctcc t gcctcattt   64500
ctctccaggg tgatgctgac agggacactg tctgaccggc agccggctga a ctccacctc   64560
ttccggaact acgatgctcc agaaactgtc cgggagcctc gtttcaacca g aacgttaac   64620
ctcaggcctc cagctcagcc ctcaggttta accatgttt gatgcatcca t gggaagcga   64680
ctggcccgag aggctgtggg gtggtgggtg ggagtcgtgc acttgccatc a ggcaccctc   64740
accgtgccac cagcccaccc gctgcactgg tctttattgg ctgaggacag g gattgcggg   64800
ggagctgtca ggcccctggc aggttagaaa agtccctgga aagtcctcag c tgtacctgc   64860
cttccaccag gacgaactag ccagagagtg tggcttcgtg ggtcctgctt c tgaagagtt   64920
cccagcctcc cctcttcccg cacccccagc ccccaacacg cacaccctga g atctggagt   64980
gcatgggttt tatgccagtc ccttgtgcca ctgggccgcc ctccttcccc g ccctagac    65040
cagctggtgt ggcgggcggc ccgaagcagc ggggcagctc ctacttactt c cgacccaat   65100
gggcgcttcc tggacggtgg gctgctggcc aacaacccca cgctggatgc c atgaccgag   65160
atccatgagt acaatcagga cctgatccgc aaggtgagtg ccgtaggcca g agggcctgg   65220
acccactgct ccctggagcc aatcctgtgt cagcaaacca tgctagggac c gaccccccag  65280
gacagcaggt ggcttttaca cacgcactca ttcatatgtg cacacagggc a aattgatct   65340
cactggaacc tgttccatgg gtgggatctg cctgaagcac tgtgctaagg g ggatctgag   65400
gaccactgtg ctctaagtgt gcatgagtgg ggagggcggc atgcatacca t gaacgtgcc   65460
actcgagcca gcctggggac aggacacatg cttgcccttg agctcacctc t gtggataga   65520
cagtcccaca ggaatgcctg tcccacgggg ttgccggtgc tgtggtggag g accgtgagg   65580
cctctgctaa aaggcctggg ggctcggaaa gggctccatg gaacagggga c ccatcctga   65640
ggcccttggg gacagagcag tgcagaatca gtgatctgga ggaagagcag c agccctctc   65700
tctgcagagg tacagcagag gctggcagga cccagcatgc tagggaggc c ctgtggcgt    65760
ggcgggcggt gggtgaccgg ggtgggcgag cgcggtggct gagctcagac c ctggagcca   65820
gggcgcctct gggggtcccc gttctgcctg cactcactgc agctacctaa t ggggccatc   65880
atagcgcctg cctggggagg ctgcgaggcc ttggcatgct gttgtctgtg a aatgttcac   65940
agcactgccg ggagcctgag ctgcatcctt gctgctgtgg tttcccgaag c cccagggcg   66000
tcctgggcag cgcagcagag gctctgggca gacagagaag cgccctctag g gccagatc    66060
gggcagggcg ggcttcctgc aggcggcaga gaccgtcaga ctgtcagaca c tagccagtc   66120
taactctcct attgcgtgcg gatgggagc ctgggaccca gagtgggagg c atcacccaa   66180
gatcatccag caaatcggca gcagagcttg ttcgaagca aataagagag g cagcggccg    66240
ggcgcagcgg ctcacgcctg taatcccagc actttgggag gccgaggcaa g tggatcatg   66300
```

```
aggtcaggag atcgagacca tcctggctaa cacggtgaaa ccctgtctct a ctaaaaata  66360 caaaaaaatt agccaggcgg gcatagtggc aggagcctgt agtcccagct a ctcgggatg  66420 ctgaggcagg agaatggtgt gaacccagga ggcgagctt  gcagtgagcc g agatcgcgc  66480 cactgcactc cagactggga gacagagcga gactccgtct caaaaaaaaa a aaaaaaagg  66540 cagcacccag ggctcaggtt caagccttag cccctacttc cctaccacgt g gccctgca   66600 gctgcttccc ggcctgagct tcgctgagag ccctcatttg caaactgggt g atcagtgcc  66660 ctctccacag actggctgga gattaaatga agtaatgatg caaatacctg g caaatcacc  66720 aacaccaagg aacaccgtct gcctttcctc ccctggccac gacttgactt g gccagcat   66780 cagatggggt gggcgggatc cttcttgcag ctggtgtatg tgtggtcctg t tggtacaca  66840 gatgctgtcc tgagcagatg gcatgtgatg cccgcaccag ccgttctggg g tcacgtgca  66900 agaggctggc tggaaatcat gccaggcatg ctcttgccac cagagacctc t tgccctgtt  66960 ctcatgtgcc ccagagccca gtcttgggcc tcccttgac  gctccccttc g tgcccccta  67020 cctgtggaag gtctcttctg actgccctg  tcctgttccc aacagggtca g gccaacaag  67080 gtgaagaaac tctccatcgt tgtctccctg gggacaggga ggtccccaca a gtgcctgtg  67140 acctgtgtga atgtcttccg tcccagcaac ccctgggagc tggccaagac t gttttggg   67200 gccaaggaac tgggcaagat ggtggtggac tgtgtgagtg tgggcccctc c cccaggcca  67260 cttccctcag ggtctgtagc ccaggtcgat ggcttcccct catcctgtgg g gcctttggt  67320 gttggaggag acagcagggc tctgtccatc gcctttagcc agctggaggg a gagagagtc  67380 cacagttcag agtctcagtg cggggcaggg accctcagtg accaccagca g gggggtttt  67440 caaacgcttt ttagctgcgg atcccttct  gcaaacatag cgcagtgtag a agcccagaa  67500 tggacaaagg ctccagagcg ggctgggcgc tcaccctgta atcccagcac t ttgggaggc  67560 caaggcaggc ggaccacttg agcacagcag tttgagacca gcctgagcaa t ataatgaga  67620 ctttgtctct accaaaaaat taaaaactag ctggacatgg tggtgtgtgc c tgtggtccc  67680 agctactcag gaggctgagg tgggaggatt gcttaagccc aagaggcaga g gctgcagtg  67740 agctgtgatc atgccactgc actccagcct gagcaacaga aggagacctt g tctcaaaaa  67800 gaaagaaaga aagagagaga gagagagaga ggagggaggg agggaaactt c agggagagg  67860 ggacatggag gcctgtcgac tcagccgcta ccctttcccc cactcatcat c cctgaaagg  67920 gcactgctga gacctctgcc cctctgattg cacagctggg acagtccctg c agtcccagg  67980 aagggttttt gcccgagccg ctctgctgct gtgtggctca gcctgactcg a aagagcctg  68040 ggctccca  ggctggggct ccgagagtgc agggcagggc cggcgggt   g cggccgggg  68100 cggggtgtgg gcccggcact caccaaggct gcttctcacc agtgcacgga t ccagacggg  68160 cgggctgtgg accgggcacg ggcctggtgc gagatggtcg gcatccagta c ttcaggtga  68220 gggctcagcc gccccagccc ttggccccgt gccctggcgt ggtcggactc a ccgaccttc  68280 ccctcccagc cctagtgtgg acttcccctt cccaagggt  ctgctctgtt c cccaagccc  68340 accctggtcc tagctggcgt cccctgccca gcctgagcat cctagggtga c ccctcctc   68400 cctgcccga  acagattgaa  cccccagctg gggacggaca tcatgctgga t gaggtcagt  68460 gacacagtgc tggtcaacgc cctctgggag accgaggtct acatctatga g caccgcgag  68520 gagttccaga agctcatcca gctgctgctc tcaccctgag ggtccccagc c tctcaccgg  68580 ccccagctga cctcgtccat tcagcccctg ccaggccaag cccagccact g ccctcccgg  68640
```

```
gcagatctgg gcccaggcac ctctgagtcc atagaccagg cctgggagaa t gccaagctg   68700 cctgcccgag gctggtcctg aaggcctgtc tcccactaac cccgccttcc a gcactttct   68760 gtcattccag gctgggaaag tctagagccc cctttggccc ctttccctga c tgtcaagga   68820 caactgactc ccccatcagc tcaaacatta agggtacccg ggcacaaccg t accectgcc   68880 cccagcccca gctccctga gggcctgccg ggctgcctct gccccagccc c cagcaaggg   68940 cactcccagg cttcctggtg ggtgcagccc actccctctg ccctctgctc c gttccctgg   69000 gggctgggac taaagaaatg ggtgtccccc accccatcag ctgggaaagc c caggccgca   69060 ggagtgggat gcccgttgga ctttgcccct cacactggcc cagcccctca c actgcccca   69120 ccccgagaac cctcagctct caaaggtcac tcctgggagt ttcttcttcc c aatggaagt   69180 ggcttaagag ccaaaactga aataaatcat ttggattcaa gttcacctgt g ttgtgtgtg   69240 cagtggtgtg agatccacct gttccccctga ccccgcgctc cctcggcct t gacccttgg   69300 ccttgaccgg acttttcctt tgtacccgga cactctgttt tccaggatcc c tgggcaggg   69360 acacctcctc tttcctctag gcctccccta aaccggccct tagggtatgc a gaggcagct   69420 gccaggccca catacccccg gcaggcccaa ggagggccac aatcttcaac t tcatcttgg   69480 aggaccaggg agagccccat ttgtcaccca gagaggccgg ggactccgcg t ggacaggca   69540 gcgcgtgtgc agggccgagg tctgcccagg gctgggcaac tccagcgttt g tgctgctcc   69600 tgctccggca gtggaggag ctgggcgggc cagagcggct gtgggagcca a gctcagagg   69660 gcgtggcccc actgtgagcc gcaggcctga ggacagtgag aagtaaagcg g cgttcccct   69720 ccaggggctg ctgctgctgg gtctggcaga gagagtcctg ggggagggca t cgggcagcg   69780 cccgcccagt aagtgggca atgcctggta taggcaggtg ggagggcggg g ccccccagg   69840 gttggggtcc ttgaggaggg ggtgacccag gagggggctc atccacatgg g cacttgtat   69900 cagcccacag ctccaagggg tgaataattg aagggcaggt cacacgagcc t gcccggcac   69960 aggatgcctt ccctgccgga tctggttacg ccccagatca                           70000
```

<210> SEQ ID NO 4
<211> LENGTH: 23
<212> TYPE: DNA
<213> ORGANISM: Artificial Sequence
<220> FEATURE:
<223> OTHER INFORMATION: PCR Primer

<400> SEQUENCE: 4
ggcgtcacca acttgttctc taa                                              23

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
cggtcactcg aggtgtagtc g                                                21

<210> SEQ ID NO 6
<211> LENGTH: 23
<212> TYPE: DNA
<213> ORGANISM: Artificial Sequence
<220> FEATURE:
<223> OTHER INFORMATION: PCR Probe

<400> SEQUENCE: 6

```
cattccgggt gaaggaggtg gct                                               23

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                    19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                   20

<210> SEQ ID NO 10
<211> LENGTH: 3240
<212> TYPE: DNA
<213> ORGANISM: Homo sapiens
<220> FEATURE:
<221> NAME/KEY: unsure
<222> LOCATION: 2770
<223> OTHER INFORMATION: unknown
<223> OTHER INFORMATION:
<221> NAME/KEY: CDS
<222> LOCATION: (137)...(2557)

<400> SEQUENCE: 10 ctggggtcc gttccccaac ttcctcggcg ctccggactc ccaagtctcc g ccggaccct       60 cctttggata ttcctcgtgt ctccgattct gagagagggg gaagacggtg g ggcctcccc    120 acctgccccg cagaag atg cag ttc ttt ggc cgc ctg gtc aat acc ttc agt     172
               Met Gln Phe Phe Gly Arg Leu Val Asn Thr P he Ser
                 1               5                  10 ggc gtc acc aac ttg ttc tct aac cca ttc c gg gtg aag gag gtg gct       220
Gly Val Thr Asn Leu Phe Ser Asn Pro Phe A rg Val Lys Glu Val Ala
         15                  20                   25 gtg gcc gac tac acc tcg agt gac cga gtt c gg gag gaa ggg cag ctg       268
Val Ala Asp Tyr Thr Ser Ser Asp Arg Val A rg Glu Glu Gly Gln Leu
     30                  35                    40 att ctg ttc cag aac act ccc aac cgc acc t gg gac tgc gtc ctg gtc       316
Ile Leu Phe Gln Asn Thr Pro Asn Arg Thr T rp Asp Cys Val Leu Val
 45                  50                   55                  60 aac ccc agg aac tca cag agt gga ttc cga c tc ttc cag ctg gag ttg       364
Asn Pro Arg Asn Ser Gln Ser Gly Phe Arg L eu Phe Gln Leu Glu Leu
             65                   70                   75 gag gct gac gcc cta gtg aat ttc cat cag t at tct tcc cag ctg cta       412
```

-continued

```
                    Glu Ala Asp Ala Leu Val Asn Phe His Gln Tyr Ser Ser Gln Leu Leu
                                80                  85                  90 ccc ttc tat gag agc tcc cct cag gtc ctg cac act gag gtc ctg cag                         460
Pro Phe Tyr Glu Ser Ser Pro Gln Val Leu His Thr Glu Val Leu Gln
             95                  100                 105 cac ctg acc gac ctc atc cgt aac cac ccc agc tgg tca gtg gcc cac                         508
His Leu Thr Asp Leu Ile Arg Asn His Pro Ser Trp Ser Val Ala His
    110                 115                 120 ctg gct gtg gag cta ggg atc cgc gag tgc ttc cat cac agc cgt atc                         556
Leu Ala Val Glu Leu Gly Ile Arg Glu Cys Phe His His Ser Arg Ile
125                 130                 135                 140 atc agc tgt gcc aat tgc gcg gag aac gag gag ggc tgc aca ccc ctg                         604
Ile Ser Cys Ala Asn Cys Ala Glu Asn Glu Glu Gly Cys Thr Pro Leu
                145                 150                 155 cac ctg gcc tgc cgc aag ggt gat ggg gag atc ctg gtg gag ctg gtg                         652
His Leu Ala Cys Arg Lys Gly Asp Gly Glu Ile Leu Val Glu Leu Val
            160                 165                 170 cag tac tgc cac act cag atg gat gtc acc gac tac aag gga gag acc                         700
Gln Tyr Cys His Thr Gln Met Asp Val Thr Asp Tyr Lys Gly Glu Thr
        175                 180                 185 gtc ttc cat tat gct gtc cag ggt gac aat tct cag gtg ctg cag ctc                         748
Val Phe His Tyr Ala Val Gln Gly Asp Asn Ser Gln Val Leu Gln Leu
    190                 195                 200 ctt gga agg aac gca gtg gct ggc ctg aac cag gtg aat aac caa ggg                         796
Leu Gly Arg Asn Ala Val Ala Gly Leu Asn Gln Val Asn Asn Gln Gly
205                 210                 215                 220 ctg acc ccg ctg cac ctg gcc tgc cag ctg ggg aag cag gag atg gtc                         844
Leu Thr Pro Leu His Leu Ala Cys Gln Leu Gly Lys Gln Glu Met Val
                225                 230                 235 cgc gtg ctg ctg ctg tgc aat gct cgg tgc aac atc atg ggc ccc aac                         892
Arg Val Leu Leu Leu Cys Asn Ala Arg Cys Asn Ile Met Gly Pro Asn
            240                 245                 250 ggc tac ccc atc cac tcg gcc atg aag ttc tct cag aag ggg tgt gcg                         940
Gly Tyr Pro Ile His Ser Ala Met Lys Phe Ser Gln Lys Gly Cys Ala
        255                 260                 265 gag atg atc atc agc atg gac agc agc cag atc cac agc aaa gac ccc                         988
Glu Met Ile Ile Ser Met Asp Ser Ser Gln Ile His Ser Lys Asp Pro
    270                 275                 280 cgt tac gga gcc agc ccc ctc cac tgg gcc aag aac gca gag atg gcc                         1036
Arg Tyr Gly Ala Ser Pro Leu His Trp Ala Lys Asn Ala Glu Met Ala
285                 290                 295                 300 cgc atg ctg ctg aaa cgg ggc tgc aac gtg aac agc acc agc tcc gcg                         1084
Arg Met Leu Leu Lys Arg Gly Cys Asn Val Asn Ser Thr Ser Ser Ala
                305                 310                 315 ggg aac acg gcc ctg cac gtg gcg gtg atg cgc aac cgc ttc gac tgt                         1132
Gly Asn Thr Ala Leu His Val Ala Val Met Arg Asn Arg Phe Asp Cys
            320                 325                 330 gcc ata gtg ctg ctg acc cac ggg gcc aac gcg gat gcc cgc gga gag                         1180
Ala Ile Val Leu Leu Thr His Gly Ala Asn Ala Asp Ala Arg Gly Glu
        335                 340                 345 cac ggc aac acc ccg ctg cac ctg gcc atg tcg aaa gac aac gtg gag                         1228
His Gly Asn Thr Pro Leu His Leu Ala Met Ser Lys Asp Asn Val Glu
    350                 355                 360 atg atc aag gcc ctc atc gtg ttc gga gca gaa gtg gac acc ccg aat                         1276
Met Ile Lys Ala Leu Ile Val Phe Gly Ala Glu Val Asp Thr Pro Asn
365                 370                 375                 380 gac ttt ggg gag act cct aca ttc cta gcc tcc aaa atc ggc aga ctt                         1324
Asp Phe Gly Glu Thr Pro Thr Phe Leu Ala Ser Lys Ile Gly Arg Leu
                385                 390                 395
```

```
                                                              -continued gtc acc agg aag gcg atc ttg act ctg ctg a ga acc gtg ggg gcc gaa       1372
Val Thr Arg Lys Ala Ile Leu Thr Leu Leu A rg Thr Val Gly Ala Glu
            400                 405                 410 tac tgc ttc cca ccc atc cac ggg gtc ccc g cg gag cag ggc tct gca       1420
Tyr Cys Phe Pro Pro Ile His Gly Val Pro A la Glu Gln Gly Ser Ala
            415                 420                 425 gcg cca cat cat ccc ttc tcc ctg gaa aga g ct cag ccc cca ccg atc       1468
Ala Pro His His Pro Phe Ser Leu Glu Arg A la Gln Pro Pro Pro Ile
430                 435                 440 agc cta aac aac cta gaa cta cag gat ctc a tg cac atc tca cgg gcc       1516
Ser Leu Asn Asn Leu Glu Leu Gln Asp Leu M et His Ile Ser Arg Ala
445                 450                 455                 460 cgg aag cca gcg ttc atc ctg ggc tcc atg a gg gac gag aag cgg acc       1564
Arg Lys Pro Ala Phe Ile Leu Gly Ser Met A rg Asp Glu Lys Arg Thr
            465                 470                 475 cac gac cac ctg ctg tgc ctg gat gga gga g ga gtg aaa ggc ctc atc       1612
His Asp His Leu Leu Cys Leu Asp Gly Gly G ly Val Lys Gly Leu Ile
            480                 485                 490 atc atc cag ctc ctc atc gcc atc gag aag g cc tcg ggt gtg gcc acc       1660
Ile Ile Gln Leu Leu Ile Ala Ile Glu Lys A la Ser Gly Val Ala Thr
            495                 500                 505 aag gac ctg ttt gac tgg gtg gcg ggc acc a gc act gga ggc atc ctg       1708
Lys Asp Leu Phe Asp Trp Val Ala Gly Thr S er Thr Gly Gly Ile Leu
510                 515                 520 gcc ctg gcc att ctg cac agt aag tcc atg g cc tac atg cgc ggc atg       1756
Ala Leu Ala Ile Leu His Ser Lys Ser Met A la Tyr Met Arg Gly Met
525                 530                 535                 540 tac ttt cgc atg aag gat gag gtg ttc cgg g gc tcc agg ccc tac gag       1804
Tyr Phe Arg Met Lys Asp Glu Val Phe Arg G ly Ser Arg Pro Tyr Glu
            545                 550                 555 tcg ggg ccc ctg gag gag ttc ctg aag cgg g ag ttt ggg gag cac acc       1852
Ser Gly Pro Leu Glu Glu Phe Leu Lys Arg G lu Phe Gly Glu His Thr
            560                 565                 570 aag atg acg gac gtc agg aaa ccc aag gtg a tg ctg aca ggg aca ctg       1900
Lys Met Thr Asp Val Arg Lys Pro Lys Val M et Leu Thr Gly Thr Leu
            575                 580                 585 tct gac cgg cag ccg gct gaa ctc cac ctc t tc cgg aac tac gat gct       1948
Ser Asp Arg Gln Pro Ala Glu Leu His Leu P he Arg Asn Tyr Asp Ala
590                 595                 600 cca gaa act gtc cgg gag cct cgt ttc aac c ag aac gtt aac ctc agg       1996
Pro Glu Thr Val Arg Glu Pro Arg Phe Asn G ln Asn Val Asn Leu Arg
605                 610                 615                 620 cct cca gct cag ccc tca gac cag ctg gtg t gg cgg gcg gcc cga agc       2044
Pro Pro Ala Gln Pro Ser Asp Gln Leu Val T rp Arg Ala Ala Arg Ser
                    625                 630                 635 agc ggg gca gct cct act tac ttc cga ccc a at ggg cgc ttc ctg gac       2092
Ser Gly Ala Ala Pro Thr Tyr Phe Arg Pro A sn Gly Arg Phe Leu Asp
                640                 645                 650 ggt ggg ctg ctg gcc aac aac ccc acg ctg g at gcc atg acc gag atc       2140
Gly Gly Leu Leu Ala Asn Asn Pro Thr Leu A sp Ala Met Thr Glu Ile
            655                 660                 665 cat gag tac aat cag gac ctg atc cgc aag g gt cag gcc aac aag gtg       2188
His Glu Tyr Asn Gln Asp Leu Ile Arg Lys G ly Gln Ala Asn Lys Val
            670                 675                 680 aag aaa ctc tcc atc gtt gtc tcc ctg ggg a ca ggg agg tcc cca caa       2236
Lys Lys Leu Ser Ile Val Val Ser Leu Gly T hr Gly Arg Ser Pro Gln
685                 690                 695                 700 gtg cct gtg acc tgt gtg gat gtc ttc cgt c cc agc aac ccc tgg gag       2284
Val Pro Val Thr Cys Val Asp Val Phe Arg P ro Ser Asn Pro Trp Glu
            705                 710                 715
```

-continued

| | | |
|---|---|---|
| ctg gcc aag act gtt ttt ggg gcc aag gaa c tg ggc aag atg gtg gtg<br>Leu Ala Lys Thr Val Phe Gly Ala Lys Glu L eu Gly Lys Met Val Val<br>720                 725                 730 | | 2332 |
| gac tgt tgc acg gat cca gac ggg cgg gct g tg gac cgg gca cgg gcc<br>Asp Cys Cys Thr Asp Pro Asp Gly Arg Ala V al Asp Arg Ala Arg Ala<br>735                 740                 745 | | 2380 |
| tgg tgc gag atg gtc ggc atc cag tac ttc a ga ttg aac ccc cag ctg<br>Trp Cys Glu Met Val Gly Ile Gln Tyr Phe A rg Leu Asn Pro Gln Leu<br>750                 755                 760 | | 2428 |
| ggg acg gac atc atg ctg gat gag gtc agt g ac aca gtg ctg gtc aac<br>Gly Thr Asp Ile Met Leu Asp Glu Val Ser A sp Thr Val Leu Val Asn<br>765                 770                 775                 780 | | 2476 |
| gcc ctc tgg gag acc gag gtc tac atc tat g ag cac cgc gag gag ttc<br>Ala Leu Trp Glu Thr Glu Val Tyr Ile Tyr G lu His Arg Glu Glu Phe<br>785                 790                 795 | | 2524 |
| cag aag ctc atc cac ctg ctc ctc tca ccc t ga gggtcccag cctctcaccg<br>Gln Lys Leu Ile His Leu Leu Leu Ser Pro<br>800                 805 | | 2577 |
| gccccagctg acctcgtcca ttcagcccct gccaggccaa gcccagccac t gccctcccg | | 2637 |
| ggcagatctg ggcccaggca cctctgagtc catagaccag gcctgggaga a tgccaagct | | 2697 |
| gcctgcccga ggctggtcct gaaggcctgt ctcccactaa ccccccttc c atcactttc | | 2757 |
| tgtcatgcca ggntgggaaa gtctagagcc ccctttggcc cctttccctg a ctgtcaagg | | 2817 |
| acaactgact cccccatcag ctcaaacatt aagggtaccc gggcacaacc g tacccgtgc | | 2877 |
| ccccagcccc agcctaccct gagggcctgc cgggctgcct ttgccccagc c cccagcaag | | 2937 |
| ggcattccca ggcttcctgg tgggtgcagc ccaatccctc tgccctctgc t ccgttccct | | 2997 |
| gggggctggg actaaagaaa tgggtgtccc ccaccccatc agctgggaaa g cccaggccg | | 3057 |
| caggagtggg atgcccgttg gactttgccc ctcacactgg cccagcccct c acactgccc | | 3117 |
| caccccgaga accctcagct ctcaaaggtc actcctggga gtttcttctt c ccaatggaa | | 3177 |
| gtggcttaag agccaaaact gaaataaatc atttggattc aagttcaaaa a aaaaaaaa | | 3237 |
| aaa | | 3240 |

<210> SEQ ID NO 11
<211> LENGTH: 2296
<212> TYPE: DNA
<213> ORGANISM: Homo sapiens
<220> FEATURE:

<400> SEQUENCE: 11

| | |
|---|---|
| cttctagata ttacaacaat cttgtattac tgtgcccact tcctggatga t gggtctgag | 60 |
| gttcacagag atcatttgcc caagttccta ctgaaagtgc taaggtattt c ctgagactg | 120 |
| gctcagggtg tgttgccaga caacaatgca cacatttta acacaatact a aacttagta | 180 |
| tattatactt atgttaaaaa tttcggagcc gggcgtggtg gctcacgcct g taatcccag | 240 |
| cacttcggga ggctgaggcg ggcagatcac ttgaggtcag gagttcgaga c cagcctggc | 300 |
| caacatggtg aaaccccgtc tctactaaaa atacaaaaaa ttagctgggc g tagtggcgg | 360 |
| gcgcctgcaa tctcagctac gcgggaggct gacgcaggag aatcgcttga a tccgggagg | 420 |
| cggaggttgc agtgagcgag atcgtgccac tgcactccag catggtcgac a gagcgagac | 480 |
| ttgtctcaaa aaaaaaaaaa aaaggacatg tggtaattc ccctagggaa t ttggcctta | 540 |
| gttgtgaaaa ataaaaagc tataatcaat ttctgttcta tcggaaaaaa t gtattggc | 600 |
| tgtttagctg aaattcaaat gtaacttaac atcccgtatt ttttatatgc t acatctggc | 660 |

```
aaccctggct tgaggctacc tggcaaaaat caaaacaggt tcctccttgt t atgccctat    720 gcctctgttg cctttatttt tatctttacg agcaatcatt aacagtaact t cagactcca    780 ggctctggtc gctttaggag gcggaaggcg gactagggta ggactcctgg c cctcatcaa    840 caggactgcc aagaagccgg gcaccttctg ccccgcacaa acatggccgc g cctcgccgc    900 cgaggattgg ctcccgccga agctcgtcc tcctggctaa gggagcccct t ccattgggc     960 agttaaaaaa aatggcggac cccgcctccc gccgtcctcg ggcgcggggg c ggagcctag   1020 aggaggcctg ggacagggcc accagtgatt ggcgagagc ggtggtcagg c catcacgtg    1080 gcccgaggcc cgtttgtttg cggaagtagg aggaagtaga agtgctgagt a agccgaggt   1140 gagtgacctc gcgggtgggc ggggcctggg ggtccgttcc ccaacttcct c ggcgctccg   1200 gactcccaag tctccgccgg accctccttt ggatattcct cgtgtctccg a ttctgaggc   1260 atgtcctcca ttaacccta tgtgactccc tgagtgcccc caccttccat c ttttcatcc    1320 ccctgcgtcc ccaattccca tcccgagacc gcccgtgtct catctcgaac t tgtggaccc   1380 cagggacccc agcttcgacc ctgagtttct ccctgaacc ccagtctcct c cgtgtgtct    1440 ccctcagtat ccctaacttc ccgagtcaat ccatctcttc tctttccccg a ccctcagtg   1500 cctctttagg ccccattggc cgtcctaatt ttccttcctg tgctcctcta a gtgctcact   1560 tgattcccca cttcacgtcc gtctccacct ttcgtggtgc ctctactcat t tctcactcc   1620 ctgcttctcc tgcctttcct ccctgctttt tttccttgcc tttcctctct c gcgtgcctc   1680 cagacctgcc cccgacatgc tccctccttc ccctcagcct ggccacccca g agtctccca   1740 cccctaatcc tgtgtccacc tcctgctccc acagatgact tggaagctgg t gacagggag   1800 catgtgacca gggtgatcat gggactgggt cggggcaagc ctgtgggtgt g ggacaggga   1860 gggcacaggg caaggggacc tgtggccgta tttttaatgg gctacccaca t gaccccaac   1920 gaatacctcc ccctagcttc tgggtctttc cctcacctgc ctcttacccg c ccaacagga   1980 tgtcaggcag gttcggtttg gcaacgttga ggctgcaccc ttgggctgaa t gcattgttt   2040 ttgaatgcat tgttttttgtt agagtttctg cctggagttt ggaacctgtt t tctgtccaa   2100 gtctcagttt cctcatctgt gcagggaa ctgtacctcc tgccctcgta a gtctgccat    2160 gaggttcaaa atttgaatga gaaatgtag aaggtaaagc tttataacca g tatggccct   2220 gtacaaatac atgattttac tgttgggtca taggcagaat tgaaaggagt g gaaagggaa   2280 agggctagaa tgagaa                                                    2296

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
aaaaccaagc ttgcctgctg                                                 20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
```
ggtgtagtcg gccacagcca                                                20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
cctggctaag agtagatggt                                                20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
agtatctatg ctatcatagt                                                20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
gctcaatcac aaattgcaaa                                                20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
atacctgtaa tcccaccact                                                20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tggtctccca aagtgctggg                                                20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gggaaggcat cctgtgccgg                                                20

<210> SEQ ID NO 20
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 20
acacgaggaa tatccaaagg                                          20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tcagaatcgg agacacgagg                                          20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
aagaactgca tcttctgcgg                                          20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tccttcaccc ggaatgggtt                                          20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
atccactctg tgagttcctg                                          20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ctggaagagt cggaatccac                                          20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
actgatggaa attcactagg                                          20
```

```
<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
atgaggtcgg tcaggtgctg                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
cggctgtgat ggaagcactc                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tcacccttgc ggcaggccag                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
accagctcca ccaggatctc                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gtctctccct tgtagtcggt                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tggacagcat aatggaagac                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 33
tgtggatctg gctgctgtcc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ctgcgttctt ggcccagtgg                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cagcatgcgg gccatctctg                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ctgttcacgt tgcagccccg                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
cggagctggt gctgttcacg                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tgcagggccg tgttccccgc                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ttcgacatgg ccaggtgcag                                              20

<210> SEQ ID NO 40
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
agtctgccga ttttggaggc                                           20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ctggtgacaa gtctgccgat                                           20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gagctctttc cagggagaag                                           20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gtgcatgaga tcctgtagtt                                           20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cgcttctcgt ccctcatgga                                           20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
caggtggtcg tgggtccgct                                           20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
```
tggatgatga tgaggccttt                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
aggccttctc gatggcgatg                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
aatggccagg gccaggatgc                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tacatgccgc gcatgtaggc                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
aacacctcat ccttcatgcg                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gtgtgctccc caaactcccg                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ttggtgtgct ccccaaactc                                              20

<210> SEQ ID NO 53
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 53
cagcatcacc ttgggtttcc                                             20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gtcagcatca ccttgggttt                                             20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
cagtgtccct gtcagcatca                                             20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
cagacagtgt ccctgtcagc                                             20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gctgccggtc agacagtgtc                                             20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tggagcatcg tagttccgga                                             20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
accagctggt ctgagggctg                                             20
```

```
<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
taagtaggag ctgccccgct                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tgggtcggaa gtaagtagga                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gggttgttgg ccagcagccc                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
tactcatgga tctcggtcat                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tcctgattgt actcatggat                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cccagggaga caacgatgga                                               20

<210> SEQ ID NO 66
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 66
ggacggaaga catccacaca                          20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
aacagtcttg gccagctccc                          20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
atcttgccca gttccttggc                          20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
aacagtccac caccatcttg                          20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gatccgtgca acagtccacc                          20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tggatccgtg caacagtcca                          20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gccgaccatc tcgcaccagg                          20

```
<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
agtactggat gccgaccatc                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tctgaagtac tggatgccga                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
actgacctca tccagcatga                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ctcggtctcc cagagggcgt                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
agatgtagac ctcggtctcc                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ctcatagatg tagacctcgg                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 79
cggtgctcat agatgtagac                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ggaccctcag ggtgagagca                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
caggcctggt ctatggactc                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
accagcctcg ggcaggcagc                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
cacccaccag gaagcctggg                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
catttcttta gtcccagccc                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cggcctgggc tttcccagct                                               20

<210> SEQ ID NO 86
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 86
atcccactcc tgcggcctgg                                            20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
caggagtgac ctttgagagc                                            20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
ttgaatccaa atgatttatt                                            20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tactggttat aaagctttac                                            20
```

ANTISENSE MODULATION OF PHOSPHOLIPASE A2, GROUP VI (CA2+-INDEPENDENT) EXPRESSION

FIELD OF THE INVENTION

The present invention provides compositions and methods for modulating the expression of Phospholipase A2, group VI (Ca2+-independent). In particular, this invention relates to compounds, particularly oligonucleotides, specifically hybridizable with nucleic acids encoding Phospholipase A2, group VI (Ca$^{2+}$-independent). Such compounds have been shown to modulate the expression of Phospholipase A2, group VI (Ca2+-independent).

BACKGROUND OF THE INVENTION

The enzymes of the phospholipase A2 (PLA2) family catalyze hydrolysis of the sn-2 fatty acid bond of phospholipids to liberate free fatty acids and lysophospholipids. These metabolites are involved in diverse cellular processes including signal transduction, host defense (including antibacterial effects), formation of platelet activating cofactor, membrane remodeling and general lipid metabolism (Dennis, *J. Biol. Chem.*, 1994, 269, 13057–13060; Dennis, *Trends Biochem. Sci*, 1997, 22, 1–2). While the human PLA2 enzymes are of greatest interest, most of the current understanding of PLA2s has been obtained by studying enzymes from non-human sources. Since most of the human PLA2s have essentially identical non-human counterparts, the knowledge obtained from the non-human enzymes is equally applicable to the human enzymes (Dennis, *J. Biol. Chem.*, 1994, 269, 13057–13060).

PLA2s are a diverse class of enzymes with regard to function, localization, regulation, mechanism, structure and dependence on divalent metal ions for activity (Dennis, *J. Biol. Chem.*, 1994, 269, 13057–13060; Dennis, *Trends Biochem. Sci*, 1997, 22, 1–2). The PLA2s have been divided into ten groups (denoted using Roman numerals I through X) (Cupillard et al., *J. Biol. Chem.*, 1997, 272, 15745–15752; Dennis, *Trends Biochem. Sci*, 1997, 22, 1–2). The PLA2s of groups IV and VI are intracellular, high molecular weight enzymes which have not been as extensively studied as the secreted PLA2s (groups I–III, V and X) (Balsinde and Dennis, *J. Biol. Chem.*, 1997, 272, 16069–16072.). Group IV requires calcium for activity whereas the activity of group VI is calcium-independent.

First cloned from Chinese hamster ovary cells in 1997 (Tang et al., *J. Biol. Chem.*, 1997, 272, 8567–8575.), the calcium-independent phospholipase A2 (PLA2 group VI, also known as iPLA2 and PLA2G6) plays a housekeeping role in phospholipid remodeling (Balsinde and Dennis, *J. Biol. Chem.*, 1997, 272, 16069–16072.). Signaling roles in generation of substrate for leukotriene biosynthesis (Larsson Forsell et al., *FEBS Lett.*, 1998, 434, 295–299.), generation of lipid messengers involved in regulation of ion channel activity (Ma et al., *J. Biol. Chem.*, 1997, 272, 11118–11127.) and apoptosis (Atsumi et al., *J. Biol. Chem.*, 1998, 273, 13870–13877.) have also been proposed for this enzyme.

Human calcium-independent phospholipase A2 (PLA2 group VI) expressed in B-cells was found to undergo extensive alternative splicing, generating multiple isoforms that contribute to a novel catalytic control mechanism (Larsson et al., *J. Biol. Chem.*, 1998, 273, 207–214.). In addition, Ma et al. have mapped human calcium-independent phospholipase A2 (PLA2, group VI) to chromosome 22q13.1 and identified mRNA encoding two catalytically active isoforms in pancreatic islet cells. The long 88 KDa isoform is known as LH-iPLA2 while the shorter, 85 KDa protein (SH-iPLA2) is a splice variant produced by an exon-skipping mechanism (Ma et al., *J. Biol. Chem.*, 1999, 274, 9607–9616.).

Functional impairment of pancreatic islet beta cells is implicated in both type I and type II diabetes mellitus (Ma et al., *J. Biol. Chem.*, 1999, 274, 9607–9616.). In rodent islets, calcium-independent phospholipase A2 (PLA2 group VI) has been proposed to play a signaling role in glucose-induced insulin secretion (Tang et al., *J. Biol. Chem.*, 1997, 272, 8567–8575.) and in experimentally induced beta cell apoptosis (Zhou et al., *J.Clin. Invest.*, 1998, 101, 1623–1632.).

A number of small molecules have been employed as inhibitors of calcium-independent phospholipase A2 (PLA2 group VI), including: arachidonyl trifluoromethyl ketone, arachidonyl tricarbonyl and methyl arachidonyl fluorophosphonate which function as transition state analogues and bromoenol lactone which acts an irreversible mechanism-based inhibitor (Balsinde and Dennis, *J. Biol. Chem.*, 1997, 272, 16069–16072.).

An antisense phosphorothioate oligonucleotide targeting nucleotides 59–78 of murine calcium-independent phospholipase A2 (PLA2 group VI) mRNA was used to inhibit the process of phospholipid fatty acid remodeling in murine P388D1 macrophages (Balsinde et al., *J. Biol. Chem.*, 1997, 272, 29317–29321.).

Pharmacological modulation of calcium-independent phospholipase A2 (PLA2 group VI) activity and/or expression may be an appropriate point for therapeutic intervention in pathologic conditions such as diabetes mellitus types I and II and conditions related to abnormal apoptosis. To date, investigative strategies aimed at inhibiting the action of calcium-independent phospholipase A2 (PLA2 group VI) have been limited to the previously cited studies involving small molecule inhibitors and the single antisense oligonucleotide. Consequently, there remains a need for additional agents which modulate the function of this enzyme.

Antisense technology is emerging as an effective means for reducing the expression of specific gene products and may therefore prove to be uniquely useful in a number of therapeutic, diagnostic, and research applications for the modulation of calcium-independent phospholipase A2 (PLA2 group VI) expression.

The present invention provides compositions and methods for modulating calcium-independent phospholipase A2 (PLA2 group VI) expression, including modulation of the splice variant forms of calcium-independent phospholipase A2 (PLA2 group VI).

SUMMARY OF THE INVENTION

The present invention is directed to compounds, particularly antisense oligonucleotides, which are targeted to a nucleic acid encoding Phospholipase A2, group VI (Ca2+-independent), and which modulate the expression of Phospholipase A2, group VI (Ca2+-independent). Pharmaceutical and other compositions comprising the compounds of the invention are also provided. Further provided are methods of modulating the expression of Phospholipase A2, group VI (Ca2+-independent) in cells or tissues comprising contacting said cells or tissues with one or more of the antisense compounds or compositions of the invention. Further provided are methods of treating an animal, particularly a human, suspected of having or being prone to a disease or condition associated with expression of Phospholipase A2, group VI (Ca2+-independent) by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding Phospholipase A2, group VI (Ca2+-independent), ultimately modulating the amount of Phospholipase A2, group VI (Ca2+-independent) produced. This is accomplished by providing antisense compounds which specifically hybridize with one or more nucleic acids encoding Phospholipase A2, group VI (Ca2+-independent). As used herein, the terms "target nucleic acid" and "nucleic acid encoding Phospholipase A2, group VI (Ca2+-independent)" encompass DNA encoding Phospholipase A2, group VI (Ca2+-independent), RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Phospholipase A2, group VI (Ca2+-independent). In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Phospholipase A2, group VI (Ca2+-independent). The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Phospholipase A2, group VI (Ca2+-independent), regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, Aphosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted-nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position; OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2O$—$CH_2$ —$N(CH_2)_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Phospholipase A2, group VI (Ca2+-independent) is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Phospholipase A2, group VI (Ca2+-independent), enabling sandwich and other assays to easily be constructed to exploit this fact. Hybridization of the antisense oligonucleotides of the invention with a nucleic acid encoding Phospholipase A2, group VI (Ca2+-independent) can be detected by means known in the art. Such means may include conjugation of an enzyme to the oligonucleotide, radiolabelling of the oligonucleotide or any other suitable detection means. Kits using such detection means for detecting the level of Phospholipase A2, group VI (Ca2+-independent) in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred completing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, N.Y., 1996,pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al.,*J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin; calcium sulfate, ethyl cellulose, polyacrylates or calcium hydrogen phosphate, etc.); lubricants (e.g., magnesium stearate, talc, silica, colloidal silicon dioxide, stearic: acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are hot limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$ -displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.: Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCH$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/hexane/acetone (5:5:1) containing 0.5% Et$_3$NH. The pure fractions were evaporated to give 164 g of product. Approximately 20 g additional was obtained from the impure fractions: to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$'gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O -(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2C_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, b. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O-CH$_2$-O-CH$_2$-N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the:hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonudleosides, also identified as amide-3 linked oligonudleosides, and methyleneaminocarbonyl linked oligonucleosides, also identified as amide-4 linked oligonucleosides, as well as mixed backbone compounds having, for instance; alternating MMI and P=O or P=S linkages are prepared as described in U.S. Pat. Nos .5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5–23. They may also be prepared in accordance with U.S. Pat. Nos. 5,539,082, 5,700,922,and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3, H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Phospholipase A2, Group VI (Ca2+-independent) Expression Antisense modulation of Phospholipase A2, group VI (Ca2+-independent) expression can be assayed in a variety of ways known in the art. For example, Phospholipase A2, group VI (Ca2+-independent) mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Phospholipase A2,group VI (Ca2+-independent) can be quantitated in a variety of ways well known in the art, such as immunoprecipitation, Western blot analysis (immunoblotting), ELISA or fluorescence-activated cell sorting (FACS). Antibodies directed to Phospholipase A2,group VI (Ca2+-independent) can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found

Example 11

Poly(A)+ mRNA isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Phospholipase A2, group VI (Ca2+-independent) mRNA Levels Quantitation of Phospholipase A2,group VI (Ca2+-independent) mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25

Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human Phospholipase A2,group VI (Ca2+-independent) were designed to hybridize to a human Phospholipase A2,group VI (Ca2+-independent) sequence, using published sequence information (GenBank accession number AL022322_COMP_TRUNC, incorporated herein as SEQ ID NO:3). For human Phospholipase A2, group VI (Ca2+-independent) the PCR primers were:

forward primer: GGCGTCACCAACTTGTTCTCTAA (SEQ ID NO: 4) reverse primer: CGGTCACTCGAGGT-GTAGTCG (SEQ ID NO: 5) and the PCR probe was: FAM-CATTCCGGGTGAAGGAGGTGGCT-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:
forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Phospholipase A2, Group VI (Ca2+-independent) mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Phospholipase A2, group VI (Ca2+-independent), a human Phospholipase A2, group VI (Ca2+-independent) specific probe was prepared by PCR using the forward primer GGCGTCACCAACTTGTTCTCTAA (SEQ ID NO: 4) and the reverse primer CGGTCACTCGAGGT-GTAGTCG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Phospholipase A2, Group VI (Ca2+-independent) Expression by Chimeric Phosphorothioate Oligonucleotides Having 2'-MOE Wings and a Deoxy Gap In accordance with the present invention, a series of oligonucleotides were designed to target different regions of the human Phospholipase A2, group VI (Ca2+-independent) RNA, using published sequences (the complement of residues 1–70000 of GenBank accession number AL022322, incorporated herein as SEQ ID NO: 3, GenBank accession number AF064594, incorporated herein as SEQ ID NO: 10, and the complement of residues 40601–42896 of GenBank accession number AL021977, incorporated herein as SEQ ID NO: 11). The oligonucleotides are shown in Table 1. "Target site" indicates the first (5'—most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Phospholipase A2, group VI (Ca2+-independent) mRNA levels by quantitative real-time PCR as described in other examples herein. Data are averages from two experiments. If present, "N.D." indicates "no data".

TABLE 1

Inhibition of human Phospholipase A2, group VI (Ca2+-independent) mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 129845 | Intron | 3 | 7118 | aaaaccaagcttgcctgctg | 81 | 12 |
| 129846 | Intron | 3 | 11373 | ggtgtagtcggccacagcca | 70 | 13 |
| 129847 | Intron | 3 | 15023 | cctggctaagagtagatggt | 40 | 14 |
| 129848 | Intron | 3 | 16574 | agtatctatgctatcatagt | 39 | 15 |
| 129849 | Intron | 3 | 27859 | gctcaatcacaaattgcaaa | 65 | 16 |
| 129850 | Intron | 3 | 31022 | atacctgtaatcccaccact | 52 | 17 |
| 129851 | Intron | 3 | 32898 | tggtctcccaaagtgctggg | 49 | 18 |
| 129852 | Intron | 3 | 69954 | gggaaggcatcctgtgccgg | 50 | 19 |
| 129853 | 5'UTR | 10 | 61 | acacgaggaatatccaaagg | 79 | 20 |
| 129854 | 5'UTR | 10 | 73 | tcagaatcggagacacgagg | 79 | 21 |
| 129855 | Start Codon | 10 | 128 | aagaactgcatcttctgcgg | 86 | 22 |
| 129856 | Coding | 10 | 194 | tccttcacccggaatgggtt | 77 | 23 |
| 129857 | Coding | 10 | 322 | atccactctgtgagttcctg | 70 | 24 |
| 129858 | Coding | 10 | 336 | ctggaagagtcggaatccac | 61 | 25 |
| 129859 | Coding | 10 | 376 | actgatggaaattcactagg | 76 | 26 |
| 129860 | Coding | 10 | 458 | atgaggtcggtcaggtgctg | 47 | 27 |
| 129861 | Coding | 10 | 533 | cggctgtgatggaagcactc | 54 | 28 |
| 129862 | Coding | 10 | 608 | tcacccttgcggcaggccag | 65 | 29 |
| 129863 | Coding | 10 | 632 | accagctccaccaggatctc | 92 | 30 |
| 129864 | Coding | 10 | 680 | gtctctcccttgtagtcggt | 70 | 31 |
| 129865 | Coding | 10 | 701 | tggacagcataatggaagac | 73 | 32 |
| 129866 | Coding | 10 | 958 | tgtggatctggctgctgtcc | 5 | 33 |
| 129867 | Coding | 10 | 1009 | ctgcgttcttggcccagtgg | 54 | 34 |
| 129868 | Coding | 10 | 1026 | cagcatgcgggccatctctg | 51 | 35 |
| 129869 | Coding | 10 | 1052 | ctgttcacgttgcagccccg | 73 | 36 |
| 129870 | Coding | 10 | 1063 | cggagctggtgctgttcacg | 78 | 37 |
| 129871 | Coding | 10 | 1082 | tgcagggccgtgttccccgc | 63 | 38 |
| 129872 | Coding | 10 | 1196 | ttcgacatggccaggtgcag | 70 | 39 |
| 129873 | Coding | 10 | 1304 | agtctgccgattttggaggc | 68 | 40 |
| 129874 | Coding | 10 | 1313 | ctggtgacaagtctgccgat | 64 | 41 |
| 129875 | Coding | 10 | 1435 | gagctctttccagggagaag | 59 | 42 |
| 129876 | Coding | 10 | 1485 | gtgcatgagatcctgtagtt | 46 | 43 |
| 129877 | Coding | 10 | 1541 | cgcttctcgtccctcatgga | 66 | 44 |
| 129878 | Coding | 10 | 1557 | caggtggtcgtgggtccgct | 15 | 45 |
| 129879 | Coding | 10 | 1601 | tggatgatgatgaggccttt | 0 | 46 |
| 129880 | Coding | 10 | 1627 | aggccttctcgatggcgatg | 42 | 47 |
| 129881 | Coding | 10 | 1701 | aatggccagggccaggatgc | 52 | 48 |
| 129882 | Coding | 10 | 1739 | tacatgccgcatgtaggc | 56 | 49 |
| 129883 | Coding | 10 | 1763 | aacacctcatccttcatgcg | 45 | 50 |
| 129884 | Coding | 10 | 1832 | gtgtgctcccaaactcccg | 8 | 51 |
| 129885 | Coding | 10 | 1835 | ttggtgtgctcccaaactc | 77 | 52 |
| 129886 | Coding | 10 | 1869 | cagcatcaccttgggtttcc | 28 | 53 |
| 129887 | Coding | 10 | 1871 | gtcagcatcaccttgggttt | 43 | 54 |
| 129888 | Coding | 10 | 1881 | cagtgtccctgtcagcatca | 60 | 55 |
| 129889 | Coding | 10 | 1885 | cagacagtgtcctgtcagc | 70 | 56 |
| 129890 | Coding | 10 | 1894 | gctgccggtcagacagtgtc | 46 | 57 |
| 129891 | Coding | 10 | 1932 | tggagcatcgtagttccgga | 41 | 58 |
| 129892 | Coding | 10 | 2006 | accagctggtctgagggctg | 16 | 59 |
| 129893 | Coding | 10 | 2045 | taagtaggagctgccccgct | 80 | 60 |
| 129894 | Coding | 10 | 2056 | tgggtcggaagtaagtagga | 41 | 61 |
| 129895 | Coding | 10 | 2096 | gggttgttggccagcagccc | 21 | 62 |
| 129896 | Coding | 10 | 2129 | tactcatggatctcggtcat | 74 | 63 |
| 129897 | Coding | 10 | 2138 | tcctgattgtactcatggat | 59 | 64 |
| 129898 | Coding | 10 | 2198 | cccagggagacaacgatgga | 44 | 65 |
| 129899 | Coding | 10 | 2249 | ggacggaagacatccacaca | 56 | 66 |
| 129900 | Coding | 10 | 2280 | aacagtcttggccagctccc | 79 | 67 |
| 129901 | Coding | 10 | 2306 | atcttgcccagttccttggc | 71 | 68 |
| 129902 | Coding | 10 | 2320 | aacagtccaccaccatcttg | 2 | 69 |
| 129903 | Coding | 10 | 2329 | gatccgtgcaacagtccacc | 76 | 70 |
| 129904 | Coding | 10 | 2331 | tggatccgtgcaacagtcca | 22 | 71 |
| 129905 | Coding | 10 | 2379 | gccgaccatctcgcaccagg | 20 | 72 |
| 129906 | Coding | 10 | 2389 | agtactggatgccgaccatc | 53 | 73 |
| 129907 | Coding | 10 | 2394 | tctgaagtactggatgccga | 39 | 74 |
| 129908 | Coding | 10 | 2439 | actgacctcatccagcatga | 68 | 75 |
| 129909 | Coding | 10 | 2475 | ctcggtctcccagagggcgt | 72 | 76 |
| 129910 | Coding | 10 | 2485 | agatgtagacctcggtctcc | 51 | 77 |
| 129911 | Coding | 10 | 2490 | ctcatagatgtagacctcgg | 8 | 78 |
| 129912 | Coding | 10 | 2495 | cggtgctcatagatgtagac | 59 | 79 |
| 129913 | Stop Codon | 10 | 2544 | ggaccctcaggggtgagagca | 53 | 80 |
| 129914 | 3'UTR | 10 | 2663 | caggcctggtctatggactc | 20 | 81 |
| 129915 | 3'UTR | 10 | 2695 | accagcctcgggcaggcagc | 72 | 82 |

TABLE 1-continued

Inhibition of human Phospholipase A2, group VI (Ca2+-independent) mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 129916 | 3'UTR | 10 | 2944 | cacccaccaggaagcctggg | 0 | 83 |
| 129917 | 3'UTR | 10 | 3000 | catttctttagtcccagccc | 67 | 84 |
| 129918 | 3'UTR | 10 | 3038 | cggcctgggctttcccagct | 32 | 85 |
| 129919 | 3'UTR | 10 | 3050 | atcccactcctgcggcctgg | 16 | 86 |
| 129920 | 3'UTR | 10 | 3135 | caggagtgacctttgagagc | 58 | 87 |
| 129921 | 3'UTR | 10 | 3200 | ttgaatccaaatgatttatt | 46 | 88 |
| 129922 | Intron | 11 | 2194 | tactggttataaagctttac | 90 | 89 |

As shown in Table 1, SEQ ID NOs 12, 13, 14, 16, 17, 18, 19, 20, 21, 22, 23, 24, 25, 26, 27, 28, 29, 30, 31, 32, 34, 35, 36, 37, 38, 39, 40, 41, 42, 43, 44, 47, 48, 49, 50, 52, 54, 55, 56, 57, 58, 60, 61, 63, 64, 65, 66, 67, 68, 70, 73, 75, 77, 79, 80, 82, 84, 87, 88 and 89 demonstrated at least 40% inhibition of human Phospholipase A2, group VI (Ca2+-independent) expression in this assay and are therefore preferred. The target sites to which these preferred sequences are complementary are herein referred to as "active sites" and are therefore preferred sites for targeting by compounds of the present invention.

Example 16

Western Blot Analysis of Phospholipase A2, Group VI (Ca2+-independent) protein levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Phospholipase A2, group VI (Ca2+-independent) is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound up to 50 nucleobases in length comprising at least an 8-nucleobase portion of SEQ ID NO: 12, 13, 14, 16, 17, 18, 19, 20, 21, 22, 24, 25, 26, 27, 28, 29, 30, 31, 32, 34, 35, 36, 37, 38, 39, 40, 41, 42, 43, 44, 47, 48, 49, 50, 52, 54, 55, 56, 57, 58, 60, 61, 63, 64, 65, 66, 67, 68, 70, 73, 75, 76, 77, 79, 80, 82, 84, 87, 88 or 89 which inhibits the expression of Phospholipase A2, group VI (Ca2+-independent).

2. The compound of claim 1 which is an antisense oligonucleotide.

3. The compound of claim 2, wherein the antisense oligonucleotide comprises at least one modified internucleoside linkage.

4. The compound of claim 3, wherein the modified internucleoside linkage is a Phosphorothioate linkage.

5. The compound of claim 2, wherein the antisense oligonucleotide comprises at least one modified sugar moiety.

6. The compound of claim 5, wherein the modified sugar moiety is a 2'-O-methoxyethyl sugar moiety.

7. The compound of claim 2, wherein the antisense oligonucleotide comprises at least one modified nucleobase.

8. The compound of claim 7, wherein the modified nucleobase is a 5-methylcytosine.

9. The compound of claim 2, wherein the antisense oligonucleotide is a chimeric oligonucleotide.

10. A composition comprising the antisense compound of claim 1, and a pharmaceutically acceptable carrier or diluent.

11. The composition of claim 10, further comprising a colloidal dispersion system.

12. The composition of claim 10, wherein the antisense compound is an antisense oligonucleotide.

13. A method of inhibiting the expression of human Phospholipase A2, group VI (Ca2+-independent) in cells or tissues comprising contacting said cells or tissues in vitro with the compound of claim 3 so that expression of human Phospholipase A2, group VI (Ca2+-independent) is inhibited.

* * * * *